US005756307A

United States Patent [19]
Uhl et al.

[11] Patent Number: 5,756,307
[45] Date of Patent: *May 26, 1998

[54] SEQUENCE OF HUMAN DOPAMINE TRANSPORTER CDNA

[75] Inventors: George R. Uhl, Towson; David Vandenbergh, Baltimore, both of Md.

[73] Assignee: The United States of America as represented by the Department of Health and Human Services, Washington, D.C.

[*] Notice: The term of this patent shall not extend beyond the expiration date of Pat. No. 5,312,734.

[21] Appl. No.: 301,722

[22] Filed: Sep. 7, 1994

Related U.S. Application Data

[63] Continuation of Ser. No. 889,723, Jun. 1, 1992, abandoned, which is a continuation-in-part of Ser. No. 762,132, Sep. 20, 1991, Pat. No. 5,312,734.

[51] Int. Cl.[6] .............................. C12N 15/12; C12N 5/10
[52] U.S. Cl. .................. 435/69.1; 435/252.3; 435/320.1; 536/23.5
[58] Field of Search .............................. 435/69.1, 252.3, 435/320.1; 536/23.5

[56] References Cited

U.S. PATENT DOCUMENTS 5,389,543   2/1995   Bunzow et al. .

FOREIGN PATENT DOCUMENTS 9308262   4/1993   WIPO .

OTHER PUBLICATIONS

Nelson et al., *FEBS Letters* vol. 269(1):181–184, Aug. 1990.
Giros et al, FEBS Letters, vol. 295, No. 1,2,3, pp. 149–154 (1991).
Kilty et al. Science, vol. 254, p. 578 (1991).
Shimada et al. "Cloning and Expression of a . . . ", *Science*, vol. 254, Oct. 25, 1991, pp. 576–578.
Guestella et al. "Cloning and Expression of a Rat Brain . . . ", *Science*, vol. 249, Sep. 14, 1990, pp. 1303–1306.
Yamauchi et al, "Cloning of a $Na^+$-and $Cl^-$-Dependent . . . ", *J. of Bio. Chem.*, vol. 267, Jan. 5, 1992, pp. 649–652.
Pacholczyk et al. "Expression Cloning of a Cocaine-. . . ", *Nature*, vol. 350, Mar. 28, 1991, pp. 350–354.
Blakely et al. "Cloning and Expression of a Functional . . . ", *Nature*, vol. 354, Nov. 7, 1991, pp. 66–70.
Bannon et al. (1990) Journal of Neurochemistry vol. 54, No. 2 pp. 706–708.
Guastella et al. (1990) Science vol. 249:1303–1306.
Nizmik et al (1990) Archives of Biochemistry and Biophysics vol. 276, No. 2 pp. 424–432.
Ritz et al (1987) Science vol. 237:1219–1223.
Uhl et al (1991) Molecular Brain Research 9:pp. 23–29.
Blum et al, JAMA, Apr. 18, 1990—Vol. 263, No. 15, pp. 2055–2060.
Arch Gen Psychiatry—vol. 48, Jul. 1991, pp. 664–666.
Uhl et al, Arc Gen Psychiatry—vol. 49, Feb. 1992, pp. 157–160.
Smith et al, Addiction Research Center, pp. 1–20.

*Primary Examiner*—John Ulm
*Attorney, Agent, or Firm*—Fitch, Even, Tabin & Flannery

[57] ABSTRACT

The cloning and characterization of a human dopamine transporter (HUDAT) cDNA is described. RFLP analysis is used to determine the distribution of HUDAT alleles in two ethic backgrounds. The means by which the association between HUDAT alleles and behavioral disorders which have altered HUDAT expression as a basis for their etiology is discussed. Methods for evaluating the expression of HUDAT are described.

10 Claims, 10 Drawing Sheets

Fig. 1a

```
  1  GAATTCCCGC  TCTCGGGGCC  AGGACTCGCG  TGCAAAGCCC  AGGCCCGGGC
 51  GGCCAGACCA  AGAGGGAAGA  AGCACAGAAT  TCCTCAACTC  CCAGTGTGCC
101  CATGAGTAAG  AGCAAATGCT  CCGTGGGACT  CATGTCTTCC  GTGGTGGCCC
151  CGGCTAAGGA  GCCCAATGCC  GTGGGCCCGA  AGGAGGTGGA  GCTCATCCTT
201  GTCAAGGAGC  AGAACGGAGT  GCAGCTCACC  AGCTCCACCC  TCACCAACCC
251  GCGGCAGAGC  CCCGTGGAGG  CCCAGGATCG  GGAGACCTGG  GGCAAGAAGA
301  TCGACTTTCT  CCTGTCCGTC  ATTGGCTTTG  CTGTGGACCT  GGCCAACGTC
351  TGGCGGTTCC  CCTACCTGTG  CTACAAAAAT  GGTGGCGGTG  CCTTCCTGGT
401  CCCCTACCTG  CTCTTCATGG  TCATTGCTGG  GATGCCACTT  TTCTACATGG
451  AGCTGGCCCT  CGGCCAGTTC  AACAGGGAAG  GGGCCGCTGG  TGTCTGGAAG
501  ATCTGCCCCA  TACTGAAAGG  TGTGGGCTTC  ACGGTCATCC  TCATCTCACT
551  GTATGTCGGC  TTCTTCTACA  ACGTCATCAT  CGCCTGGGCG  CTGCACTATC
601  TCTTCTCCTC  CTTCACCACG  GAGCTCCCCT  GGATCCACTG  CAACAACTCC
651  TGGAACAGCC  CCAACTGCTC  GGATGCCCAT  CCTGGTGACT  CCAGTGGAGA
701  CAGCTCGGGC  CTCAAGGACA  CTTTTGGGAC  CACACCTGCT  GCCGAGTACT
751  TTGAACGTGG  CGTGCTGCAC  CTCCACCAGA  GCCATGGCAT  CGACGACCTG
```

Fig. 1

| Fig. 1a | Fig. 1b | Fig. 1c | Fig. 1d | Fig. 1e |

Fig. 1b

| | | | | |
|---|---|---|---|---|
| 801 | GGGCCTCCGC | GGTGGCAGCT | CACAGCCTGC | CTGGTGCTGG | TCATCGTGCT |
| 851 | GCTCTACTTC | AGCCTCTGGA | AGGGCGTGAA | GACCTCAGGG | AAGGTGGTAT |
| 901 | GGATCACAGC | CACCATGCCA | TACGTGGTCC | TCACTGCCCT | GCTCCTGCGT |
| 951 | GGGGTCACCC | TCCTGGAGC | CATAGAGCAT | ATCAGAGCAT | ACCTGAGCGT |
| 1001 | TGACTTCTAC | CGGCTCTGCG | AGGCGTCTGT | TTGGATTGAC | GCGGCCACCC |
| 1051 | AGGTGTGCTT | CTCCCTGGGC | GTGGGGTTCG | GGGTGCTGAT | CGCCTTCTCC |
| 1101 | AGCTACAACA | AGTTCACCAA | CAACTGCTAC | AGGGACGGGA | TTGTCACCAC |
| 1151 | CTCCATCAAC | TCCCTGACGA | GCTTCTCCTC | CGGCTTCGTC | GTCTTCTCCT |
| 1201 | TCCTGGGGTA | CATGGCACAG | AAGCACAGTG | TGCCCATCGG | GGACGTGGCC |
| 1251 | AAGGACGGGC | CAGGGCTGAT | CTTCATCATC | TACCCGGAAG | CCATCGCCAC |
| 1301 | GCTCCCTCTG | TCCTCAGCCT | GGGCCGTGGT | CTTCTTCATC | ATGCTGCTCA |
| 1351 | CCCTGGGTAT | CGACAGCGCC | ATGGGTGGTA | TGGAGTCAGT | GATCACCGGG |
| 1401 | CTCATCGATG | AGTTCCAGCT | GCTGCACAGA | CACCGTGAGC | TCTTCACGCT |
| 1451 | CTTCATCGTC | CTGGCGACCT | TCCTCCTGTC | CCTGTTCTGC | GTCACCAACG |
| 1501 | GTGGCATCTA | CGTCTTCACG | CTCCTGGACC | ATTTTGCAGC | CGGCACGTCC |
| 1551 | ATCCTCTTTG | GAGTGCTCAT | CGAAGCCATC | GGAGTGGCCT | GGTTCTATGG |

Fig. 1c

| 1601 | TGTTGGGCAG | TTCAGCGACG | ACATCCAGCA | GATGACCGGG | CAGCGGCCCA |
| 1651 | GCCTGTACTG | GCGGCTGTGC | TGGAAGCTGG | TCAGCCCCTG | CTTTCTCCTG |
| 1701 | TTCGTGGTCG | TGGTCAGCAT | TGTGACCTTC | AGACCCCCC  | ACTACGGAGC |
| 1751 | CTACATCTTC | CCCGACTGGG | CCAACGCGCT | GGGCTGGGTC | ATCGCCACAT |
| 1801 | CCTCCATGGC | CATGGTGCCC | ATCTATGCGG | CCTACAAGTT | CTGCAGCCTG |
| 1851 | CCTGGGTCCT | TTCGAGAGAA | ACTGGCCTAC | GCCATTGCAC | CCGAGAAGGA |
| 1901 | CCGTGAGCTG | GTGGACAGAG | GGGAGGTGCG | CCAGTTCACG | CTCCGCCACT |
| 1951 | GGCTCAAGGT | GTAGAGGGAG | CAGAGACGAA | GACCCCAGGA | AGTCATCCTG |
| 2001 | CAATGGGAGA | GACACGAACA | AACCAAGGAA | ATCTAAGTTT | CGAGAGAAAG |
| 2051 | GAGGGCAACT | TCTACTCTTC | AACCTCTACT | GAAAACACAA | ACAACAAAGC |
| 2101 | AGAAGACTCC | TCTCTTCTGA | CTGTTTACAC | CTTTCCGTGC | GGGAGGGCA  |
| 2151 | CCTCGCCGTG | TCTTGTGTTG | CTGTAATAAC | GACGTAGATC | TGTGCAGCGA |
| 2201 | GGTCCACCCC | GTTGTTGTCC | CTGCAGGGCA | GAAAAACGTC | TAACTTCATG |
| 2251 | CTGTCTGTGT | GAGGCTCCCT | CCCTCCCTGC | TCCCTGCTCC | CGGCTCTGAG |
| 2301 | GCTGCCCAG  | GGCACTGTG  | TTCTCAGGCG | GGGATCAGGA | TCCTTGTAGA |
| 2351 | CGCACCTGCT | GAGAATCCCC | GTGCTCACAG | TAGCTTCCTA | GACCATTTAC |

```
2401  TTTGCCCATA  TTAAAAAGCC  AAGTGTCCTG  CTTGGTTTAG  CTGTGCAGAA
2451  GGTGAAATGG  AGGAAACCAC  AAATTCATGC  AAAGTCCTTT  CCGGATGCGT
2501  GGCTCCCAGC  AGAGGCCGTA  AATTGAGCGT  TCAGTTGACA  CATTGCACAC
2551  ACAGTCTGTT  CAGAGGCATT  GGAGGATGGG  GGTCCTGGTA  TGTCTCACCA
2601  GGAAATTCTG  TTTATGTTCT  TGCAGCAGAG  AGAAATAAAA  CTCCTTGAAA
2651  CCAGCTCAGG  CTACTGCCAC  TCAGGCAGCC  TGTGGGTCCT  TGTGGTGTAG
2701  GGAACGGCCT  GAGAGGAGCG  TGTCCTATCC  CCGGACGCAT  GCAGGGCCCC
2751  CACAGGAGCG  TGTCCTATCC  CCGGACGCAT  GCAGGGCCCC  CACAGGAGCA
2801  TGTCCTATCC  CTGGACGCAT  GCAGGGCCCC  CACAGGAGCG  TGTACTACCC
2851  CAGAACGCAT  GCAGGGCCCC  CACAGGAGCG  TGTACTACCC  CAGGACGCAT
2901  GCAGGGCCCC  CACTGGAGCG  TGTCCTATCC  CCGGACCGGA  GCAGGGCCCC
2951  CACAGGAGCG  TGTCCTATCC  CCGGACCGGA  CGCATGCAGG  GCCCCACAG
3001  GAGCGTGTAC  TACCCCAGGA  CGCATGCAGG  GCCCCCACAG  GAGCGTGTAC
3051  TACCCCAGGA  TGCATGCAGG  GCCCCCACAG  GAGCGTGTAC  TACCCCAGGA
3101  CGCATGCAGG  GCCCCCATGC  AGGCAGCCTG  CAGACCAACA  CTCTGCCTGG
3151  CCTTGAGCCG  TGACCTCCAG  GAAGGGACCC  CACTGGAATT  TTATTTCT
```

| 3201 | CAGGTGCGTG | CCACATCAAT | AACAACAGTT | TTTATGTTTG | CGAATGGCTT |
| --- | --- | --- | --- | --- | --- |
| 3251 | TTTAAAATCA | TATTTACCTG | TGAATCAAAA | CAAATTCAAG | AATGCAGTAT |
| 3301 | CCGCGAGCCT | GCTTGCTGAT | ATTGCAGTTT | TTGTTTACAA | GAATAATTAG |
| 3351 | CAATACTGAG | TGAAGGATGT | TGGCCAAAAG | CTGCTTTCCA | TGGCACACTG |
| 3401 | CCCTCTGCCA | CTGACAGGAA | AGTGGATGCC | ATAGTTTGAA | TTCATGCCTC |
| 3451 | AAGTCGGTGG | GCCTGCCTAC | GTGCTGCCCC | AGGGCAGGGG | CCGTGCAGGG |
| 3501 | CCAGTCATGG | CTGTCCCCTG | CAAGTGGACG | TGGGCTCCAG | GGACTGGAGT |
| 3551 | GTAATGCTCG | GTGGGAGCCC | TCAGCCTGTG | AACTGCCAGG | CAGCTGCAGT |
| 3601 | TAGCACAGAG | GATGGCTTCC | CCATTGCCTT | CTGGGGAGGG | ACACAGAGGA |
| 3651 | CGGCTTCCCC | ATCGCCTTCT | GGCGGCTGCA | GTCAGCACAG | AGAGGGGCTT |
| 3701 | CCCCATTGCC | TTCTGGGGAG | GGACACAGAG | GACAGTTTCC | CCATCGCCTT |
| 3751 | CTGGTTGTTG | AAGACAGCAC | AGAGAGCGGC | TTCCCCATCG | CCTTCTGGGG |
| 3801 | AGGGGCTCCG | TGTAGCAACC | CAGGTGTTGT | CCGTGTCTGT | TGACCAATCT |
| 3851 | CTATTCAGCA | TCGTGTGGGT | CCCTAAGCAC | AATAAAGAC | ATCCACAATG |
| 3901 | GAAAAAAAA | AAGGAATTC | | | |

*Fig. 2*

| | | | |
|---|---|---|---|
| AGGAGCGTGT | CCTATCCCCG | GACGCATGCA | GGGCCCCAC |
| AGGAGCGTGT | CCTATCCCCG | GACGCATGCA | GGGCCCCAC |
| AGGAGCATGT | CCTATCCCTG | GACGCATGCA | GGGCCCCAC |
| AGGAGCGTGT | ACTACCCCAG | AACGCATGCA | GGGCCCCAC |
| AGGAGCGTGT | ACTACCCCAG | GACGCATGCA | GGGCCCCAC |
| TGGAGCGTGT | ACTACCCCAG | GACGCATGCA | GGGCCCCAC |
| AGGAGCGTGT | CCTATCCCCG | GACCGGACGC | ATGCAGGGCC CCCAC |
| AGGAGCGTGT | ACTACCCCAG | GACGCATGCA | GGGCCCCAC |
| AGGAGCGTGT | ACTACCCCAG | GATGCATGCA | GGGCCCCAC |
| AGGAGCGTGT | ACTACCCCAG | GACGCATGCA | GGGCCCCAT |

CONSENSUS:

AGGAGCGTGT  ACTATCCCAG  GACGCATGCA  GGGCCCCAC

Fig. 3a

```
                                                                                                    50
       1    ..MSKSKCSV  GLMSSVVAPA  KEPNAVGPKE  VELILVKEQN  GVQLTSSTLT
Hdat        ..........  .P........  .S......R.  A..LV.....  .....N....
Rdat        MLLARMNPQ.  QPENNGADTG  P.QPLRAR.T  PKTLV..R..  .......C.L
Hnat        ..MATNGSK.  A..DGQISTE  VSEAP.ANDK  .....V.K..  ..........
Hgabat 100
       51   NPRQSPVEAQ  DRETWGKKID  FLLSVIGFAV  DLANVWRFPY  LCYKNGGGAF
Hdat        ...P.T....  E.........  ..........  ..........  ..........
Rdat        A..DG..D..  .....S....  .....V....  ..........  ..........
Hnat        ......KAADLP  P..D..KGRF.  ..M.CV.Y.I  G.G.......  .....G....
Hgabat 150
       101  LVPYLLFMVI  AGMPLFYMEL  ALGQFNREGA  AGVWKICPIL  KGVGFTVILI
Hdat        ...I..T.LI.  ..........  ..........  ..........  ..........
Rdat        ..........  ..........  ......Y...  .....V....  ..YA......
Hnat        ..I..F.TLIF  ..VPLFLLEC  .SLGQYTSIGG  ..T....FF  KGVGLAAAVL
Hgabat                              LGVWKLAPMF

*  +200
       151  SLYVGFFYNV  IIAWALHYLF  SSFTTELPWI  HCNNSWNSPN  CSDAHPGDSS
Hdat        .F........  ......S.Y.  .....M....  .......T..  ........ASN
Rdat        AL...Y....  ..S..IY..Y  N......T..  .D.GHT....  ..T.PKLLNG.
Hnat        SFWLNIY.I.  ..........  N......T..K  Q.D.P..TDR
Hgabat                                          *

250
       201  *G.DSSGLNDT  FGTTPA.AEY  FERGVLHLHQ  SHGIDDLGPP  RWQLTACLVL
Hdat        ...GL.....  ..........  .Y......E  ..R.......  ..Q....L.L.MV
Rdat        VLGNHTKYSK  YKF.......  ..........  .S..H.I.L.  .L.KP.QI
Hnat        FSNYSMVN.  TNM.S.VV.F  W..NMHQMTD  ..........  ..P.AIT.AI
Hgabat
```

Fig. 3b

```
        251                                                                    300
Hdat    VIVLLYFSLW  KGVKTSGKVV  WITATMPYVV  LTALLLRGVT  LPGAIDGIRA
Rdat    .VIV......  ..........  ...L.F....  .FV..VH...  .M........
Hnat    AWILV..CI.  ......GWT.  YFS.Y...IM  .II.FFR...  .SN..N....
Hgabat  ..........  ..........  ..........  ..........  .KE..LF...

301                                                                    350
Hdat    YLSVDFYRLC  EASVWIDAAT  QVCFSLGVGF  GVLIAFSSYN  KFTNNCYRDA
Rdat    .LL.S....C  ..T.......  ...IF..A..  ........S.  ..........
Hnat    ..HI...K..  .DSE.L....  ..IF..Y.L.L  ......LG..  .S.HN.V..S
Hgabat  .ITPN.RK.S  ..........  ..........  ..........  ..........

351                                                                    400
Hdat    IVTTSINSLT  SFSSGFVVFS  FLGYMAQKHS  VPIGDVAKDG  PGLIFIIYPE
Rdat    .I........  ..V.AI....  ......N...  ....R..T..  .A..V..L..
Hnat    LL.S..CI..  ..........  .I...HE.K.  ..N.E..TE.  ..........
Hgabat  .IVCC...C.  .MFA....I.  IV.F..HVTK  RS.A...AS.  ..A..LA...

401                                                                    450
Hdat    AIATLPLSSA  WAVVFFIMLL  TLGIDSAMGG  MESVITGLID  EF.QLLHRHR
Rdat    ..........  ..A...L...  ..A..L.S..  ..........  ..........
Hnat    ..S..SG.TF  ....V.....  .M.....QFCT  V.GF..A.V.  .D..V.K...
Hgabat  .VTQ.I.PL.  ..IL..S...  ..........  ..A...D...  EYPR..RNR.

451                                                                    500
Hdat    ELFTLFIVLA  TFLLSLFCVT  NGGIYVFTLL  DHF.AAGTSI  LFGVLIEAIG
Rdat    ...G......  ..........  ..........  ..........  ..........
Hnat    K..FGVTFS.  ..A.I.....  .K....L..F  .T........  ..A..M....
Hgabat  ...IAAVCII  SY.IG.SNI.  ..Q.......  YYS.S.M.L  .L.FF.CVS
```

```
             501
             VAWFYGVGQF  SDDIQQMTG Q  RPSLYWRLCW  KLVSPCFLLF  VVVSIVTFR
                                                              550
Hdat         ..........  ..........   ..........  ..........  .........
Rdat         ......Q...  .K........   .Y........  .F..A.....  ....IN.K.
Hnat         .S....DR..  .N...M.F..   ..G.......  SFFT.IIVAG  .FIF.A.QMT
Hgabat       IS.....NR.  Y.N..E.V.S   ..CIW.K...

551
             PPHYGAYIFP  DWANALGWVI   ATSSMAMVPI  YAAYKFCSLP  GSFREKLAYA
                                                              600
Hdat         ..........  ..........   ..........  ..........  ..........
Rdat         .LT.DD...P  .I........   ...L...VL.  .T......VI  .LW.R....G
Hnat         .LTM.N.V..  .P..W...G.   ...L....VL  ...L.TQ.M.  .M.LA.K...
Hgabat                   K.GQGV..LM   ....VLI.G              .LKQRIQVM 601
             IAPEKDRELV  DRGEVRQFTL   RHWLKV
Hdat         ..........  ..........   ......
Rdat         .T....HQ..  .AQRDI..Q.   ..LL..
Hnat         .T..NEHH..  .EN.PEHAQAG  Q..AI.
Hgabat       VQ.SE.TVRP               SSTS.EAYI
                                            636
```

Fig. 3

| Fig. 3a | Fig. 3b | Fig. 3c | ns

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 3919 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( v i ) ORIGINAL SOURCE:

(A) ORGANISM: Homo sapiens
(F) TISSUE TYPE: brainstem (ix) FEATURE:
  (A) NAME/KEY: CDS
  (B) LOCATION: 102..1961
  (D) OTHER INFORMATION: /function="dopamine transport"
      / product= "HUDAT polypeptide, see Fig. 5 (Hdat)

(ix) FEATURE:
  (A) NAME/KEY: misc_RNA
  (B) LOCATION: 2724..3117
  (D) OTHER INFORMATION: /function="unknown"
      / label= VNTR_region (xi) SEQUENCE DESCRIPTION: SEQ ID NO:1:

```
GAATTCCCGC TCTCGGCGCC AGGACTCGCG TGCAAAGCCC AGGCCCGGGC GGCCAGACCA           60

AGAGGGAAGA AGCACAGAAT TCCTCAACTC CCAGTGTGCC C ATG AGT AAG AGC             113
                                             Met Ser Lys Ser
                                              1

AAA TGC TCC GTG GGA CTC ATG TCT TCC GTG GTG GCC CCG GCT AAG GAG           161
Lys Cys Ser Val Gly Leu Met Ser Ser Val Val Ala Pro Ala Lys Glu
 5              10              15                   20

CCC AAT GCC GTG GGC CCG AAG GAG GTG GAG CTC ATC CTT GTC AAG GAG           209
Pro Asn Ala Val Gly Pro Lys Glu Val Glu Leu Ile Leu Val Lys Glu
                 25              30                  35

CAG AAC GGA GTG CAG CTC ACC AGC TCC ACC CTC ACC AAC CCG CGG CAG           257
Gln Asn Gly Val Gln Leu Thr Ser Ser Thr Leu Thr Asn Pro Arg Gln
         40              45                  50

AGC CCC GTG GAG GCC CAG GAT CGG GAG ACC TGG GGC AAG AAG ATC GAC           305
Ser Pro Val Glu Ala Gln Asp Arg Glu Thr Trp Gly Lys Lys Ile Asp
         55              60                  65

TTT CTC CTG TCC GTC ATT GGC TTT GCT GTG GAC CTG GCC AAC GTC TGG           353
Phe Leu Leu Ser Val Ile Gly Phe Ala Val Asp Leu Ala Asn Val Trp
 70              75                  80

CGG TTC CCC TAC CTG TGC TAC AAA AAT GGT GGC GGT GCC TTC CTG GTC           401
Arg Phe Pro Tyr Leu Cys Tyr Lys Asn Gly Gly Gly Ala Phe Leu Val
 85              90                  95                  100

CCC TAC CTG CTC TTC ATG GTC ATT GCT GGG ATG CCA CTT TTC TAC ATG           449
Pro Tyr Leu Leu Phe Met Val Ile Ala Gly Met Pro Leu Phe Tyr Met
                 105                 110                 115

GAG CTG GCC CTC GGC CAG TTC AAC AGG GAA GGG GCC GCT GGT GTC TGG           497
Glu Leu Ala Leu Gly Gln Phe Asn Arg Glu Gly Ala Ala Gly Val Trp
         120                 125                 130

AAG ATC TGC CCC ATA CTG AAA GGT GTG GGC TTC ACG GTC ATC CTC ATC           545
Lys Ile Cys Pro Ile Leu Lys Gly Val Gly Phe Thr Val Ile Leu Ile
         135                 140                 145

TCA CTG TAT GTC GGC TTC TTC TAC AAC GTC ATC ATC GCC TGG GCG CTG           593
Ser Leu Tyr Val Gly Phe Phe Tyr Asn Val Ile Ile Ala Trp Ala Leu
 150                 155                 160

CAC TAT CTC TTC TCC TCC TTC ACC ACG GAG CTC CCC TGG ATC CAC TGC           641
His Tyr Leu Phe Ser Ser Phe Thr Thr Glu Leu Pro Trp Ile His Cys
165                 170                 175                 180

AAC AAC TCC TGG AAC AGC CCC AAC TGC TCG GAT GCC CAT CCT GGT GAC           689
Asn Asn Ser Trp Asn Ser Pro Asn Cys Ser Asp Ala His Pro Gly Asp
                 185                 190                 195

TCC AGT GGA GAC AGC TCG GGC CTC AAC GAC ACT TTT GGG ACC ACA CCT           737
Ser Ser Gly Asp Ser Ser Gly Leu Asn Asp Thr Phe Gly Thr Thr Pro
             200                 205                 210

GCT GCC GAG TAC TTT GAA CGT GGC GTG CTG CAC CTC CAC CAG AGC CAT           785
Ala Ala Glu Tyr Phe Glu Arg Gly Val Leu His Leu His Gln Ser His
             215                 220                 225

GGC ATC GAC GAC CTG GGG CCT CCG CGG TGG CAG CTC ACA GCC TGC CTG           833
```

```
Gly Ile Asp Asp Leu Gly Pro Pro Arg Trp Gln Leu Thr Ala Cys Leu
    230             235                 240

GTG CTG GTC ATC GTG CTG CTC TAC TTC AGC CTC TGG AAG GGC GTG AAG    881
Val Leu Val Ile Val Leu Leu Tyr Phe Ser Leu Trp Lys Gly Val Lys
245             250                 255                 260

ACC TCA GGG AAG GTG GTA TGG ATC ACA GCC ACC ATG CCA TAC GTG GTC    929
Thr Ser Gly Lys Val Val Trp Ile Thr Ala Thr Met Pro Tyr Val Val
                265                 270                 275

CTC ACT GCC CTG CTC CTG CGT GGG GTC ACC CTC CCT GGA GCC ATA GAC    977
Leu Thr Ala Leu Leu Leu Arg Gly Val Thr Leu Pro Gly Ala Ile Asp
            280                 285                 290

GGC ATC AGA GCA TAC CTG AGC GTT GAC TTC TAC CGG CTC TGC GAG GCG   1025
Gly Ile Arg Ala Tyr Leu Ser Val Asp Phe Tyr Arg Leu Cys Glu Ala
        295                 300                 305

TCT GTT TGG ATT GAC GCG GCC ACC CAG GTG TGC TTC TCC CTG GGC GTG   1073
Ser Val Trp Ile Asp Ala Ala Thr Gln Val Cys Phe Ser Leu Gly Val
    310                 315                 320

GGG TTC GGG GTG CTG ATC GCC TTC TCC AGC TAC AAC AAG TTC ACC AAC   1121
Gly Phe Gly Val Leu Ile Ala Phe Ser Ser Tyr Asn Lys Phe Thr Asn
325             330                 335                 340

AAC TGC TAC AGG GAC GCG ATT GTC ACC ACC TCC ATC AAC TCC CTG ACG   1169
Asn Cys Tyr Arg Asp Ala Ile Val Thr Thr Ser Ile Asn Ser Leu Thr
                345                 350                 355

AGC TTC TCC TCC GGC TTC GTC GTC TTC TCC TTC CTG GGG TAC ATG GCA   1217
Ser Phe Ser Ser Gly Phe Val Val Phe Ser Phe Leu Gly Tyr Met Ala
            360                 365                 370

CAG AAG CAC AGT GTG CCC ATC GGG GAC GTG GCC AAG GAC GGG CCA GGG   1265
Gln Lys His Ser Val Pro Ile Gly Asp Val Ala Lys Asp Gly Pro Gly
        375                 380                 385

CTG ATC TTC ATC ATC TAC CCG GAA GCC ATC GCC ACG CTC CCT CTG TCC   1313
Leu Ile Phe Ile Ile Tyr Pro Glu Ala Ile Ala Thr Leu Pro Leu Ser
    390                 395                 400

TCA GCC TGG GCC GTG GTC TTC TTC ATC ATG CTG CTC ACC CTG GGT ATC   1361
Ser Ala Trp Ala Val Val Phe Phe Ile Met Leu Leu Thr Leu Gly Ile
405             410                 415                 420

GAC AGC GCC ATG GGT GGT ATG GAG TCA GTG ATC ACC GGG CTC ATC GAT   1409
Asp Ser Ala Met Gly Gly Met Glu Ser Val Ile Thr Gly Leu Ile Asp
                425                 430                 435

GAG TTC CAG CTG CTG CAC AGA CAC CGT GAG CTC TTC ACG CTC TTC ATC   1457
Glu Phe Gln Leu Leu His Arg His Arg Glu Leu Phe Thr Leu Phe Ile
            440                 445                 450

GTC CTG GCG ACC TTC CTC CTG TCC CTG TTC TGC GTC ACC AAC GGT GGC   1505
Val Leu Ala Thr Phe Leu Leu Ser Leu Phe Cys Val Thr Asn Gly Gly
        455                 460                 465

ATC TAC GTC TTC ACG CTC CTG GAC CAT TTT GCA GCC GGC ACG TCC ATC   1553
Ile Tyr Val Phe Thr Leu Leu Asp His Phe Ala Ala Gly Thr Ser Ile
    470                 475                 480

CTC TTT GGA GTG CTC ATC GAA GCC ATC GGA GTG GCC TGG TTC TAT GGT   1601
Leu Phe Gly Val Leu Ile Glu Ala Ile Gly Val Ala Trp Phe Tyr Gly
485             490                 495                 500

GTT GGG CAG TTC AGC GAC GAC ATC CAG CAG ATG ACC GGG CAG CGG CCC   1649
Val Gly Gln Phe Ser Asp Asp Ile Gln Gln Met Thr Gly Gln Arg Pro
                505                 510                 515

AGC CTG TAC TGG CGG CTG TGC TGG AAG CTG GTC AGC CCC TGC TTT CTC   1697
Ser Leu Tyr Trp Arg Leu Cys Trp Lys Leu Val Ser Pro Cys Phe Leu
            520                 525                 530

CTG TTC GTG GTC GTG GTC AGC ATT GTG ACC TTC AGA CCC CCC CAC TAC   1745
Leu Phe Val Val Val Val Ser Ile Val Thr Phe Arg Pro Pro His Tyr
        535                 540                 545

GGA GCC TAC ATC TTC CCC GAC TGG GCC AAC GCG CTG GGC TGG GTC ATC   1793
```

```
Gly Ala Tyr Ile Phe Pro Asp Trp Ala Asn Ala Leu Gly Trp Val Ile
    550                 555                 560
GCC ACA TCC TCC ATG GCC ATG GTG CCC ATC TAT GCG GCC TAC AAG TTC    1841
Ala Thr Ser Ser Met Ala Met Val Pro Ile Tyr Ala Ala Tyr Lys Phe
565                 570                 575                 580
TGC AGC CTG CCT GGG TCC TTT CGA GAG AAA CTG GCC TAC GCC ATT GCA    1889
Cys Ser Leu Pro Gly Ser Phe Arg Glu Lys Leu Ala Tyr Ala Ile Ala
                585                 590                 595
CCC GAG AAG GAC CGT GAG CTG GTG GAC AGA GGG GAG GTG CGC CAG TTC    1937
Pro Glu Lys Asp Arg Glu Leu Val Asp Arg Gly Glu Val Arg Gln Phe
            600                 605                 610
ACG CTC CGC CAC TGG CTC AAG GTG TAGAGGGAGC AGAGACGAAG ACCCCAGGAA   1991
Thr Leu Arg His Trp Leu Lys Val
        615                 620
GTCATCCTGC AATGGAGAG  ACACGAACAA ACCAAGGAAA TCTAAGTTTC GAGAGAAAGG  2051
AGGGCAACTT CTACTCTTCA ACCTCTACTG AAAACACAAA CAACAAAGCA GAAGACTCCT  2111
CTCTTCTGAC TGTTTACACC TTTCCGTGCC GGGAGCGCAC CTCGCCGTGT CTTGTGTTGC  2171
TGTAATAACG ACGTAGATCT GTGCAGCGAG GTCCACCCCG TTGTTGTCCC TGCAGGGCAG  2231
AAAAACGTCT AACTTCATGC TGTCTGTGTG AGGCTCCCTC CCTCCCTGCT CCCTGCTCCC  2291
GGCTCTGAGG CTGCCCCAGG GGCACTGTGT TCTCAGGCGG GGATCACGAT CCTTGTAGAC  2351
GCACCTGCTG AGAATCCCCG TGCTCACAGT AGCTTCCTAG ACCATTTACT TTGCCCATAT  2411
TAAAAGCCA  AGTGTCCTGC TTGGTTTAGC TGTGCAGAAG GTGAAATGGA GGAAACCACA  2471
AATTCATGCA AAGTCCTTTC CCGATGCGTG GCTCCCAGCA GAGGCCGTAA ATTGAGCGTT  2531
CAGTTGACAC ATTGCACACA CAGTCTGTTC AGAGGCATTG GAGGATGGGG GTCCTGGTAT  2591
GTCTCACCAG GAAATTCTGT TTATGTTCTT GCAGCAGAGA GAAATAAAAC TCCTTGAAAC  2651
CAGCTCAGGC TACTGCCACT CAGGCAGCCT GTGGGTCCTT GTGGTGTAGG GAACGGCCTG  2711
AGAGGAGCGT GTCCTATCCC CGGACGCATG CAGGGCCCCC ACAGGAGCGT GTCCTATCCC  2771
CGGACGCATG CAGGGCCCCC ACAGGAGCAT GTCCTATCCC TGGACGCATG CAGGGCCCCC  2831
ACAGGAGCGT GTACTACCCC AGAACGCATG CAGGGCCCCC ACAGGAGCGT GTACTACCCC  2891
AGGACGCATG CAGGGCCCCC ACTGGAGCGT GTACTACCCC AGGACGCATG CAGGGCCCCC  2951
ACAGGAGCGT GTCCTATCCC CGGACCGGAC GCATGCAGGG CCCCACAGG  AGCGTGTACT  3011
ACCCCAGGAC GCATGCAGGG CCCCACAGG  AGCGTGTACT ACCCCAGGAT GCATGCAGGG  3071
CCCCACAGG  AGCGTGTACT ACCCCAGGAC GCATGCAGGG CCCCATGCA  GGCAGCCTGC  3131
AGACCAACAC TCTGCCTGGC CTTGAGCCGT GACCTCCAGG AAGGGACCCC ACTGGAATTT  3191
TATTTCTCTC AGGTGCGTGC CACATCAATA ACAACAGTTT TTATGTTTGC GAATGGCTTT  3251
TTAAAATCAT ATTTACCTGT GAATCAAAAC AAATTCAAGA ATGCAGTATC CGCGAGCCTG  3311
CTTGCTGATA TTGCAGTTTT TGTTTACAAG AATAATTAGC AATACTGAGT GAAGGATGTT  3371
GGCCAAAAGC TGCTTTCCAT GGCACACTGC CCTCTGCCAC TGACAGGAAA GTGGATGCCA  3431
TAGTTTGAAT TCATGCCTCA AGTCGGTGGG CCTGCCTACG TGCTGCCCGA GGGCAGGGGC  3491
CGTGCAGGGC CAGTCATGGC TGTCCCCTGC AAGTGGACGT GGGCTCCAGG GACTGGAGTG  3551
TAATGCTCGG TGGGAGCCGT CAGCCTGTGA ACTGCCAGGC AGCTGCAGTT AGCACAGAGG  3611
ATGGCTTCCC CATTGCCTTC TGGGGAGGGA CACAGAGGAC GGCTTCCCCA TCGCCTTCTG  3671
GCCGCTGCAG TCAGCACAGA GAGCGGCTTC CCCATTGCCT TCTGGGGAGG GACACAGAGG  3731
ACAGTTTCCC CATCGCCTTC TGGTTGTTGA AGACAGCACA GAGAGCGGCT TCCCCATCGC  3791
CTTCTGGGGA GGGGCTCCGT GTAGCAACCC AGGTGTTGTC CGTGTCTGTT GACCAATCTC  3851
```

TATTCAGCAT CGTGTGGGTC CCTAAGCACA ATAAAAGACA TCCACAATGG AAAAAAAAA    3911

AGGAATTC    3919

( 2 ) INFORMATION FOR SEQ ID NO:2:

( i ) SEQUENCE CHARACTERISTICS:
        ( A ) LENGTH: 620 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ser | Lys | Ser | Lys | Cys | Ser | Val | Gly | Leu | Met | Ser | Ser | Val | Val | Ala |
|---|---|---|---|---|---|---|---|---|---|---|---|---|---|---|---|
| 1 |  |  |  | 5 |  |  |  |  | 10 |  |  |  |  | 15 |  |
| Pro | Ala | Lys | Glu | Pro | Asn | Ala | Val | Gly | Pro | Lys | Glu | Val | Glu | Leu | Ile |
|  |  |  | 20 |  |  |  |  | 25 |  |  |  |  | 30 |  |  |
| Leu | Val | Lys | Glu | Gln | Asn | Gly | Val | Gln | Leu | Thr | Ser | Ser | Thr | Leu | Thr |
|  |  |  | 35 |  |  |  |  | 40 |  |  |  |  | 45 |  |  |
| Asn | Pro | Arg | Gln | Ser | Pro | Val | Glu | Ala | Gln | Asp | Arg | Glu | Thr | Trp | Gly |
|  | 50 |  |  |  |  | 55 |  |  |  |  | 60 |  |  |  |  |
| Lys | Lys | Ile | Asp | Phe | Leu | Leu | Ser | Val | Ile | Gly | Phe | Ala | Val | Asp | Leu |
| 65 |  |  |  |  | 70 |  |  |  |  | 75 |  |  |  |  | 80 |
| Ala | Asn | Val | Trp | Arg | Phe | Pro | Tyr | Leu | Cys | Tyr | Lys | Asn | Gly | Gly | Gly |
|  |  |  |  | 85 |  |  |  |  | 90 |  |  |  |  | 95 |  |
| Ala | Phe | Leu | Val | Pro | Tyr | Leu | Leu | Phe | Met | Val | Ile | Ala | Gly | Met | Pro |
|  |  |  | 100 |  |  |  |  | 105 |  |  |  |  | 110 |  |  |
| Leu | Phe | Tyr | Met | Glu | Leu | Ala | Leu | Gly | Gln | Phe | Asn | Arg | Glu | Gly | Ala |
|  |  | 115 |  |  |  |  | 120 |  |  |  |  | 125 |  |  |  |
| Ala | Gly | Val | Trp | Lys | Ile | Cys | Pro | Ile | Leu | Lys | Gly | Val | Gly | Phe | Thr |
|  | 130 |  |  |  |  | 135 |  |  |  |  | 140 |  |  |  |  |
| Val | Ile | Leu | Ile | Ser | Leu | Tyr | Val | Gly | Phe | Phe | Tyr | Asn | Val | Ile | Ile |
| 145 |  |  |  |  | 150 |  |  |  |  | 155 |  |  |  |  | 160 |
| Ala | Trp | Ala | Leu | His | Tyr | Leu | Phe | Ser | Ser | Phe | Thr | Thr | Glu | Leu | Pro |
|  |  |  |  | 165 |  |  |  |  | 170 |  |  |  |  | 175 |  |
| Trp | Ile | His | Cys | Asn | Asn | Ser | Trp | Asn | Ser | Pro | Asn | Cys | Ser | Asp | Ala |
|  |  |  | 180 |  |  |  |  | 185 |  |  |  |  | 190 |  |  |
| His | Pro | Gly | Asp | Ser | Ser | Gly | Asp | Ser | Ser | Gly | Leu | Asn | Asp | Thr | Phe |
|  |  | 195 |  |  |  |  | 200 |  |  |  |  | 205 |  |  |  |
| Gly | Thr | Thr | Pro | Ala | Ala | Glu | Tyr | Phe | Glu | Arg | Gly | Val | Leu | His | Leu |
|  | 210 |  |  |  |  | 215 |  |  |  |  | 220 |  |  |  |  |
| His | Gln | Ser | His | Gly | Ile | Asp | Asp | Leu | Gly | Pro | Pro | Arg | Trp | Gln | Leu |
| 225 |  |  |  |  | 230 |  |  |  |  | 235 |  |  |  |  | 240 |
| Thr | Ala | Cys | Leu | Val | Leu | Val | Ile | Val | Leu | Leu | Tyr | Phe | Ser | Leu | Trp |
|  |  |  |  | 245 |  |  |  |  | 250 |  |  |  |  | 255 |  |
| Lys | Gly | Val | Lys | Thr | Ser | Gly | Lys | Val | Val | Trp | Ile | Thr | Ala | Thr | Met |
|  |  |  | 260 |  |  |  |  | 265 |  |  |  |  | 270 |  |  |
| Pro | Tyr | Val | Val | Leu | Thr | Ala | Leu | Leu | Leu | Arg | Gly | Val | Thr | Leu | Pro |
|  |  | 275 |  |  |  |  | 280 |  |  |  |  | 285 |  |  |  |
| Gly | Ala | Ile | Asp | Gly | Ile | Arg | Ala | Tyr | Leu | Ser | Val | Asp | Phe | Tyr | Arg |
|  | 290 |  |  |  |  | 295 |  |  |  |  | 300 |  |  |  |  |
| Leu | Cys | Glu | Ala | Ser | Val | Trp | Ile | Asp | Ala | Ala | Thr | Gln | Val | Cys | Phe |
| 305 |  |  |  |  | 310 |  |  |  |  | 315 |  |  |  |  | 320 |
| Ser | Leu | Gly | Val | Gly | Phe | Gly | Val | Leu | Ile | Ala | Phe | Ser | Ser | Tyr | Asn |
|  |  |  |  | 325 |  |  |  |  | 330 |  |  |  |  | 335 |  |

|     |     |     |     |     |     |     |     |     |     |     |     |     |     |     |
|---|---|---|---|---|---|---|---|---|---|---|---|---|---|---|
| Lys | Phe | Thr | Asn 340 | Asn | Cys | Tyr | Arg | Asp 345 | Ala | Ile | Val | Thr | Thr 350 | Ser | Ile |
| Asn | Ser | Leu 355 | Thr | Ser | Phe | Ser | Ser 360 | Gly | Phe | Val | Val | Phe 365 | Ser | Phe | Leu |
| Gly | Tyr 370 | Met | Ala | Gln | Lys | His 375 | Ser | Val | Pro | Ile | Gly 380 | Asp | Val | Ala | Lys |
| Asp 385 | Gly | Pro | Gly | Leu | Ile 390 | Phe | Ile | Ile | Tyr | Pro 395 | Glu | Ala | Ile | Ala | Thr 400 |
| Leu | Pro | Leu | Ser | Ser 405 | Ala | Trp | Ala | Val | Val 410 | Phe | Phe | Ile | Met | Leu 415 | Leu |
| Thr | Leu | Gly | Ile 420 | Asp | Ser | Ala | Met | Gly 425 | Gly | Met | Glu | Ser | Val 430 | Ile | Thr |
| Gly | Leu | Ile 435 | Asp | Glu | Phe | Gln | Leu 440 | Leu | His | Arg | His | Arg 445 | Glu | Leu | Phe |
| Thr | Leu 450 | Phe | Ile | Val | Leu | Ala 455 | Thr | Phe | Leu | Leu | Ser 460 | Leu | Phe | Cys | Val |
| Thr 465 | Asn | Gly | Gly | Ile | Tyr 470 | Val | Phe | Thr | Leu | Leu 475 | Asp | His | Phe | Ala | Ala 480 |
| Gly | Thr | Ser | Ile | Leu 485 | Phe | Gly | Val | Leu | Ile 490 | Glu | Ala | Ile | Gly | Val 495 | Ala |
| Trp | Phe | Tyr | Gly 500 | Val | Gly | Gln | Phe | Ser 505 | Asp | Asp | Ile | Gln | Gln 510 | Met | Thr |
| Gly | Gln | Arg 515 | Pro | Ser | Leu | Tyr | Trp 520 | Arg | Leu | Cys | Trp | Lys 525 | Leu | Val | Ser |
| Pro | Cys 530 | Phe | Leu | Leu | Phe | Val 535 | Val | Val | Val | Ser | Ile 540 | Val | Thr | Phe | Arg |
| Pro 545 | Pro | His | Tyr | Gly | Ala 550 | Tyr | Ile | Phe | Pro | Asp 555 | Trp | Ala | Asn | Ala | Leu 560 |
| Gly | Trp | Val | Ile | Ala 565 | Thr | Ser | Ser | Met | Ala 570 | Met | Val | Pro | Ile | Tyr 575 | Ala |
| Ala | Tyr | Lys | Phe 580 | Cys | Ser | Leu | Pro | Gly 585 | Ser | Phe | Arg | Glu | Lys 590 | Leu | Ala |
| Tyr | Ala | Ile 595 | Ala | Pro | Glu | Lys | Asp 600 | Arg | Glu | Leu | Val | Asp 605 | Arg | Gly | Glu |
| Val | Arg 610 | Gln | Phe | Thr | Leu | Arg 615 | His | Trp | Leu | Lys | Val 620 |     |     |     |     |

( 2 ) INFORMATION FOR SEQ ID NO:3:

( i ) SEQUENCE CHARACTERISTICS:
        ( A ) LENGTH: 617 amino acids
        ( B ) TYPE: amino acid
        ( C ) STRANDEDNESS: Not Relevant
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( i x ) FEATURE:
        ( A ) NAME/KEY: Protein
        ( B ) LOCATION: 1..617
        ( D ) OTHER INFORMATION: /note= "Hnat sequence, see Fig. 5"

( x i ) SEQUENCE DESCRIPTION: SEQ ID NO:3:

|     |     |     |     |     |     |     |     |     |     |     |     |     |     |     |
|---|---|---|---|---|---|---|---|---|---|---|---|---|---|---|
| Met 1 | Leu | Leu | Ala | Arg 5 | Met | Asn | Pro | Gln | Val 10 | Gln | Pro | Glu | Asn | Asn 15 | Gly |

| | | | | | | | | | | | | | |
|---|---|---|---|---|---|---|---|---|---|---|---|---|---|
| Ala | Asp | Thr | Gly 20 | Pro | Glu | Gln | Pro 25 | Arg | Ala | Arg | Lys | Thr 30 | Ala | Glu |
| Leu | Leu | Val 35 | Val | Lys | Glu | Arg | Asn 40 | Gly | Val | Gln | Cys | Leu 45 | Leu | Ala | Pro |
| Arg | Asp 50 | Gly | Asp | Ala | Gln | Pro 55 | Arg | Glu | Thr | Trp | Gly 60 | Lys | Lys | Ile | Asp |
| Phe 65 | Leu | Leu | Ser | Val | Val 70 | Gly | Phe | Ala | Val | Asp 75 | Leu | Ala | Asn | Val | Trp 80 |
| Arg | Phe | Pro | Tyr | Leu 85 | Cys | Tyr | Lys | Asn | Gly 90 | Gly | Gly | Ala | Phe | Leu 95 | Ile |
| Pro | Tyr | Thr | Leu 100 | Phe | Leu | Ile | Ile | Ala 105 | Gly | Met | Pro | Leu | Phe 110 | Tyr | Met |
| Glu | Leu | Ala | Leu 115 | Gly | Gln | Tyr | Asn | Arg 120 | Glu | Gly | Ala | Ala | Thr 125 | Val | Trp |
| Lys | Ile 130 | Cys | Pro | Phe | Phe | Lys 135 | Gly | Val | Gly | Tyr | Ala 140 | Val | Ile | Leu | Ile |
| Ala 145 | Leu | Tyr | Val | Gly | Phe 150 | Tyr | Tyr | Asn | Val | Ile 155 | Ile | Ala | Trp | Ser | Leu 160 |
| Tyr | Tyr | Leu | Phe | Ser 165 | Ser | Phe | Thr | Leu | Asn 170 | Leu | Pro | Trp | Thr | Asp 175 | Cys |
| Gly | His | Thr | Trp 180 | Asn | Ser | Pro | Asn | Cys 185 | Thr | Asp | Pro | Lys | Leu 190 | Leu | Asn |
| Gly | Ser | Val 195 | Leu | Gly | Asn | His | Thr 200 | Lys | Tyr | Ser | Lys | Tyr 205 | Lys | Phe | Thr |
| Pro | Ala 210 | Ala | Glu | Phe | Tyr | Glu 215 | Arg | Gly | Val | Leu | His 220 | Leu | His | Glu | Ser |
| Ser 225 | Gly | Ile | His | Asp | Ile 230 | Gly | Leu | Pro | Gln | Trp 235 | Gln | Leu | Leu | Leu | Cys 240 |
| Leu | Met | Val | Val | Val 245 | Ile | Val | Leu | Tyr | Phe 250 | Ser | Leu | Trp | Lys | Gly 255 | Val |
| Lys | Thr | Ser | Gly 260 | Lys | Val | Val | Trp | Ile 265 | Thr | Ala | Thr | Leu | Pro 270 | Tyr | Phe |
| Val | Leu | Phe 275 | Val | Leu | Leu | Val | His 280 | Gly | Val | Thr | Leu | Pro 285 | Gly | Ala | Ser |
| Asn | Gly 290 | Ile | Asn | Ala | Tyr | Leu 295 | His | Ile | Asp | Phe | Tyr 300 | Arg | Leu | Lys | Glu |
| Ala | Thr 305 | Val | Trp | Ile | Asp | Ala 310 | Ala | Thr | Gln | Ile 315 | Phe | Phe | Ser | Leu | Gly 320 |
| Ala | Gly | Phe | Gly | Val 325 | Leu | Ile | Ala | Phe | Ala 330 | Ser | Tyr | Asn | Lys | Phe 335 | Asp |
| Asn | Asn | Cys | Tyr 340 | Arg | Asp | Ala | Leu | Leu 345 | Thr | Ser | Ser | Ile | Asn 350 | Cys | Ile |
| Thr | Ser | Phe 355 | Val | Ser | Gly | Phe | Ala 360 | Ile | Phe | Ser | Ile | Leu 365 | Gly | Tyr | Met |
| Ala | His 370 | Glu | His | Lys | Val | Asn 375 | Ile | Glu | Asp | Val | Ala 380 | Thr | Glu | Gly | Ala |
| Gly 385 | Leu | Val | Phe | Ile | Leu 390 | Tyr | Pro | Glu | Ala | Ile 395 | Ser | Thr | Leu | Ser | Gly 400 |
| Ser | Thr | Phe | Trp | Ala 405 | Val | Val | Phe | Phe | Val 410 | Met | Leu | Leu | Ala | Leu 415 | Gly |
| Leu | Asp | Ser | Ser 420 | Met | Gly | Gly | Met | Glu 425 | Ala | Val | Ile | Thr | Gly 430 | Leu | Ala |
| Asp | Asp | Phe | Gln | Val | Leu | Lys | Arg | His | Arg | Lys | Leu | Phe | Thr | Phe | Gly |

-continued

| | | | | 435 | | | | | 440 | | | | | 445 | | | |
|---|---|---|---|---|---|---|---|---|---|---|---|---|---|---|---|---|---|
| Val | Thr 450 | Phe | Ser | Thr | Phe 455 | Leu | Ala | Leu | Phe 460 | Cys | Ile | Thr | Lys | Gly |
| Gly 465 | Ile | Tyr | Val | Leu 470 | Thr | Leu | Leu | Asp | Thr 475 | Phe | Ala | Ala | Gly | Thr | Ser 480 |
| Ile | Leu | Phe | Ala | Val 485 | Leu | Met | Glu | Ala | Ile 490 | Gly | Val | Ser | Trp | Phe 495 | Tyr |
| Gly | Val | Asp | Arg 500 | Phe | Ser | Asn | Asp | Ile 505 | Gln | Gln | Met | Met | Gly 510 | Phe | Arg |
| Pro | Gly | Leu 515 | Tyr | Trp | Arg | Leu | Cys 520 | Trp | Lys | Phe | Val | Ser 525 | Pro | Ala | Phe |
| Leu | Leu 530 | Phe | Val | Val | Val 535 | Ser | Ile | Ile | Asn | Phe 540 | Lys | Pro | Leu | Thr |
| Tyr 545 | Asp | Asp | Tyr | Ile | Phe 550 | Pro | Pro | Trp | Ala | Asn 555 | Trp | Val | Gly | Trp | Gly 560 |
| Ile | Ala | Leu | Ser | Ser 565 | Met | Val | Leu | Val | Pro 570 | Ile | Tyr | Val | Ile | Tyr 575 | Lys |
| Phe | Leu | Ser | Thr 580 | Gln | Gly | Ser | Leu | Trp 585 | Glu | Arg | Leu | Ala | Tyr 590 | Gly | Ile |
| Thr | Pro | Glu 595 | Asn | Glu | His | His | Leu 600 | Val | Ala | Gln | Arg | Asp 605 | Ile | Arg | Gln |
| Phe | Gln | Leu 610 | Gln | His | Trp | Leu 615 | Ala | Ile |

( 2 ) INFORMATION FOR SEQ ID NO:4:

( i ) SEQUENCE CHARACTERISTICS:
        ( A ) LENGTH: 619 amino acids
        ( B ) TYPE: amino acid
        ( C ) STRANDEDNESS: Not Relevant
        ( D ) TOPOLOGY: linear ( i i ) MOLECULE TYPE: protein ( i i i ) HYPOTHETICAL: NO ( v ) FRAGMENT TYPE: N-terminal ( i x ) FEATURE:
        ( A ) NAME/KEY: Protein
        ( B ) LOCATION: 1..619
        ( D ) OTHER INFORMATION: /note= "Dat1 sequence, see Fig. 5"

( x i ) SEQUENCE DESCRIPTION: SEQ ID NO:4:

| Met 1 | Ser | Lys | Ser | Lys 5 | Cys | Ser | Val | Gly | Pro 10 | Met | Ser | Ser | Val | Val 15 | Ala |
|---|---|---|---|---|---|---|---|---|---|---|---|---|---|---|---|
| Pro | Ala | Lys | Glu 20 | Ser | Asn | Ala | Val | Gly 25 | Pro | Arg | Glu | Val | Glu 30 | Leu | Ile |
| Leu | Val | Lys 35 | Glu | Gln | Asn | Gly | Val 40 | Gln | Leu | Thr | Asn | Ser 45 | Thr | Leu | Ile |
| Asn | Pro 50 | Pro | Gln | Thr | Pro | Val 55 | Glu | Ala | Gln | Glu | Arg 60 | Glu | Thr | Trp | Ser |
| Lys 65 | Lys | Ile | Asp | Phe | Leu 70 | Leu | Ser | Val | Ile | Gly 75 | Phe | Ala | Val | Asp | Leu 80 |
| Ala | Asn | Val | Trp | Arg 85 | Phe | Pro | Tyr | Leu | Cys 90 | Tyr | Lys | Asn | Gly | Gly 95 | Gly |
| Ala | Phe | Leu | Val 100 | Pro | Tyr | Leu | Leu | Phe 105 | Met | Val | Ile | Ala | Gly 110 | Met | Pro |
| Leu | Phe | Tyr 115 | Met | Glu | Leu | Ala | Leu 120 | Gly | Gln | Phe | Asn | Arg 125 | Glu | Gly | Ala |

| | | | | | | | | | | | | |
|---|---|---|---|---|---|---|---|---|---|---|---|---|
| Gly | Gly 130 | Val | Trp | Lys | Ile | Cys 135 | Pro | Val | Leu | Lys 140 | Gly | Val | Gly | Phe | Thr |
| Val 145 | Ile | Leu | Ile | Ser | Phe 150 | Tyr | Val | Gly | Phe | Phe 155 | Tyr | Asn | Val | Ile | Ile 160 |
| Ala | Trp | Ala | Leu | His 165 | Tyr | Phe | Phe | Ser | Ser 170 | Phe | Thr | Met | Asp | Leu 175 | Pro |
| Trp | Ile | His | Cys 180 | Asn | Asn | Thr | Trp | Asn 185 | Ser | Pro | Asn | Cys | Ser 190 | Asp | Ala |
| His | Ala | Ser 195 | Asn | Ser | Ser | Asp | Gly 200 | Leu | Gly | Leu | Asn | Asp 205 | Thr | Phe | Gly |
| Thr | Thr 210 | Pro | Ala | Ala | Glu | Tyr 215 | Phe | Glu | Arg | Gly | Val 220 | Leu | His | Leu | His |
| Gln 225 | Ser | Arg | Gly | Ile | Asp 230 | Asp | Leu | Gly | Pro | Pro 235 | Arg | Trp | Gln | Leu | Thr 240 |
| Ala | Cys | Leu | Val | Leu 245 | Val | Ile | Val | Leu | Leu 250 | Tyr | Phe | Ser | Leu | Trp 255 | Lys |
| Gly | Val | Lys | Thr 260 | Ser | Gly | Lys | Val | Val 265 | Trp | Ile | Thr | Ala | Thr 270 | Met | Pro |
| Tyr | Val | Val 275 | Leu | Thr | Ala | Leu | Leu 280 | Leu | Arg | Gly | Val | Thr 285 | Leu | Pro | Gly |
| Ala | Met 290 | Asp | Gly | Ile | Arg | Ala 295 | Tyr | Leu | Ser | Val | Asp 300 | Phe | Tyr | Arg | Leu |
| Cys 305 | Glu | Ala | Ser | Val | Trp 310 | Ile | Asp | Ala | Ala | Thr 315 | Gln | Val | Cys | Phe | Ser 320 |
| Leu | Gly | Val | Gly | Phe 325 | Gly | Val | Leu | Ile | Ala 330 | Phe | Ser | Ser | Tyr | Asn 335 | Lys |
| Phe | Thr | Asn | Asn 340 | Cys | Tyr | Arg | Asp | Ala 345 | Ile | Ile | Thr | Thr | Ser 350 | Ile | Asn |
| Ser | Leu | Thr 355 | Ser | Phe | Ser | Ser | Gly 360 | Phe | Val | Val | Phe | Ser 365 | Phe | Leu | Gly |
| Tyr | Met 370 | Ala | Gln | Lys | His | Asn 375 | Val | Pro | Ile | Arg | Asp 380 | Val | Ala | Thr | Asp |
| Gly 385 | Pro | Gly | Leu | Ile | Phe 390 | Ile | Ile | Tyr | Pro | Glu 395 | Ala | Ile | Ala | Thr | Leu 400 |
| Pro | Leu | Ser | Ser | Ala 405 | Trp | Ala | Ala | Val | Phe 410 | Phe | Leu | Met | Leu | Leu 415 | Thr |
| Leu | Gly | Ile | Asp 420 | Ser | Ala | Met | Gly | Gly 425 | Met | Glu | Ser | Val | Ile 430 | Thr | Gly |
| Leu | Val | Asp 435 | Glu | Phe | Gln | Leu | Leu 440 | His | Arg | His | Arg | Glu 445 | Leu | Phe | Thr |
| Leu | Gly 450 | Ile | Val | Leu | Ala | Thr 455 | Phe | Leu | Leu | Ser | Leu 460 | Phe | Cys | Val | Thr |
| Asn 465 | Gly | Gly | Ile | Tyr | Val 470 | Phe | Thr | Leu | Leu | Asp 475 | His | Phe | Ala | Ala | Gly 480 |
| Thr | Ser | Ile | Leu | Phe 485 | Gly | Val | Leu | Ile | Glu 490 | Ala | Ile | Gly | Val | Ala 495 | Trp |
| Phe | Tyr | Gly | Val 500 | Gln | Gln | Phe | Ser | Asp 505 | Asp | Ile | Lys | Gln | Met 510 | Thr | Gly |
| Gln | Arg | Pro 515 | Asn | Leu | Tyr | Trp | Arg 520 | Leu | Tyr | Trp | Lys | Leu 525 | Val | Ser | Pro |
| Cys | Phe 530 | Leu | Leu | Tyr | Val | Val 535 | Val | Val | Ser | Ile | Val 540 | Thr | Phe | Arg | Pro |
| Pro | His | Tyr | Gly | Ala | Tyr | Ile | Phe | Pro | Asp | Trp | Ala | Asn | Ala | Leu | Gly |

|     | 545 |     |     |     | 550 |     |     |     |     | 555 |     |     |     |     | 560 |
| --- | --- | --- | --- | --- | --- | --- | --- | --- | --- | --- | --- | --- | --- | --- | --- |
| Trp | Ile | Ile | Ala | Thr | Ser | Ser | Met | Ala | Met | Val | Pro | Ile | Tyr | Ala | Thr |
|     |     |     |     | 565 |     |     |     |     | 570 |     |     |     |     | 575 |     |
| Tyr | Lys | Phe | Cys | Ser | Leu | Pro | Gly | Ser | Phe | Arg | Glu | Lys | Leu | Ala | Tyr |
|     |     |     | 580 |     |     |     |     | 585 |     |     |     |     |     | 590 |     |
| Ala | Ile | Thr | Pro | Glu | Lys | Asp | His | Gln | Leu | Val | Asp | Arg | Gly | Glu | Val |
|     |     | 595 |     |     |     |     | 600 |     |     |     |     | 605 |     |     |     |
| Arg | Gln | Phe | Thr | Leu | Arg | His | Trp | Leu | Leu | Leu |     |     |     |     |     |
|     | 610 |     |     |     |     | 615 |     |     |     |     |     |     |     |     |     |

( 2 ) INFORMATION FOR SEQ ID NO:5:

( i ) SEQUENCE CHARACTERISTICS:
        ( A ) LENGTH: 599 amino acids
        ( B ) TYPE: amino acid
        ( C ) STRANDEDNESS: Not Relevant
        ( D ) TOPOLOGY: linear ( i i ) MOLECULE TYPE: protein ( i i i ) HYPOTHETICAL: NO ( v ) FRAGMENT TYPE: N-terminal ( i x ) FEATURE:
        ( A ) NAME/KEY: Protein
        ( B ) LOCATION: 1..599
        ( D ) OTHER INFORMATION: /note= "Hgabat sequence, see Fig. 5"

( x i ) SEQUENCE DESCRIPTION: SEQ ID NO:5:

| Met | Ala | Thr | Asn | Gly | Ser | Lys | Val | Ala | Asp | Gly | Gln | Ile | Ser | Thr | Glu |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Val | Ser | Glu | Ala | Pro | Val | Ala | Asn | Asp | Lys | Pro | Lys | Thr | Leu | Val | Val |
|     |     |     | 20 |     |     |     |     | 25 |     |     |     |     | 30 |     |     |
| Lys | Val | Gln | Lys | Lys | Ala | Ala | Asp | Leu | Pro | Asp | Arg | Asp | Thr | Trp | Lys |
|     |     | 35 |     |     |     |     | 40 |     |     |     |     | 45 |     |     |     |
| Gly | Arg | Phe | Asp | Phe | Leu | Met | Ser | Cys | Val | Gly | Tyr | Ala | Ile | Gly | Leu |
|     | 50 |     |     |     |     | 55 |     |     |     |     | 60 |     |     |     |     |
| Gly | Asn | Val | Trp | Arg | Phe | Pro | Tyr | Leu | Cys | Gly | Lys | Asn | Gly | Gly | Gly |
| 65 |     |     |     |     | 70 |     |     |     |     | 75 |     |     |     |     | 80 |
| Ala | Phe | Leu | Ile | Pro | Tyr | Phe | Leu | Thr | Leu | Ile | Phe | Ala | Gly | Val | Pro |
|     |     |     |     | 85 |     |     |     |     | 90 |     |     |     |     | 95 |     |
| Leu | Phe | Leu | Leu | Glu | Cys | Ser | Leu | Gly | Gln | Tyr | Thr | Ser | Ile | Gly | Gly |
|     |     |     | 100 |     |     |     |     | 105 |     |     |     |     | 110 |     |     |
| Leu | Gly | Val | Trp | Lys | Leu | Ala | Pro | Met | Phe | Lys | Gly | Val | Gly | Leu | Ala |
|     |     | 115 |     |     |     |     | 120 |     |     |     |     | 125 |     |     |     |
| Ala | Ala | Val | Leu | Ser | Phe | Trp | Leu | Asn | Ile | Tyr | Tyr | Ile | Val | Ile | Ile |
|     | 130 |     |     |     |     | 135 |     |     |     |     | 140 |     |     |     |     |
| Ser | Trp | Ala | Ile | Tyr | Tyr | Leu | Tyr | Asn | Ser | Phe | Thr | Thr | Thr | Leu | Pro |
| 145 |     |     |     |     | 150 |     |     |     |     | 155 |     |     |     |     | 160 |
| Trp | Lys | Gln | Cys | Asp | Asn | Pro | Trp | Asn | Thr | Asp | Arg | Cys | Phe | Ser | Asn |
|     |     |     |     | 165 |     |     |     |     | 170 |     |     |     |     | 175 |     |
| Tyr | Ser | Met | Val | Asn | Thr | Thr | Asn | Met | Thr | Ser | Ala | Val | Val | Glu | Phe |
|     |     |     | 180 |     |     |     |     | 185 |     |     |     |     | 190 |     |     |
| Trp | Glu | Arg | Asn | Met | His | Gln | Met | Thr | Asp | Gly | Leu | Asp | Lys | Pro | Gly |
|     |     | 195 |     |     |     |     | 200 |     |     |     |     | 205 |     |     |     |
| Gln | Ile | Arg | Trp | Pro | Leu | Ala | Ile | Thr | Leu | Ala | Ile | Ala | Trp | Ile | Leu |
|     | 210 |     |     |     |     | 215 |     |     |     |     | 220 |     |     |     |     |
| Val | Tyr | Phe | Cys | Ile | Trp | Lys | Gly | Val | Gly | Trp | Thr | Gly | Lys | Val | Val |

|     |     |     |     |     |     |     |     |     |     |     |     |     |     |     |
|-----|-----|-----|-----|-----|-----|-----|-----|-----|-----|-----|-----|-----|-----|-----|
| 225 |     |     |     |     | 230 |     |     |     |     | 235 |     |     |     | 240 |
| Tyr | Phe | Ser | Ala | Thr | Tyr | Pro | Tyr | Ile | Met | Leu | Ile | Ile | Leu | Phe |
|     |     |     |     | 245 |     |     |     |     | 250 |     |     |     | 255 |     |
| Phe | Arg | Gly | Val | Thr | Leu | Pro | Gly | Ala | Lys | Glu | Gly | Ile | Leu | Phe |
|     |     |     |     | 260 |     |     |     |     | 265 |     |     |     | 270 |     |
| Tyr | Ile | Thr | Pro | Asn | Phe | Arg | Lys | Leu | Ser | Asp | Ser | Glu | Val | Trp |
|     |     |     |     | 275 |     |     |     |     | 280 |     |     |     | 285 |     |
| Leu | Asp | Ala | Ala | Thr | Gln | Ile | Phe | Phe | Ser | Tyr | Gly | Leu | Gly | Leu |
|     |     |     |     | 290 |     |     |     |     | 295 |     |     |     | 300 |     |
| Gly | Ser | Leu | Ile | Ala | Leu | Gly | Ser | Tyr | Asn | Ser | Phe | His | Asn | Asn |
|     |     |     |     | 305 |     |     |     |     | 310 |     |     |     | 315 |     |
| Val | Tyr | Arg | Asp | Ser | Ile | Ile | Val | Cys | Cys | Ile | Asn | Ser | Cys | Thr |
|     |     |     |     | 320 |     |     |     |     | 325 |     |     |     | 330 |     |
| Ser | Met | Phe | Ala | Gly | Phe | Val | Ile | Phe | Ser | Ile | Val | Gly | Phe | Met |
|     |     |     |     | 335 |     |     |     |     | 340 |     |     |     | 345 |     |
| Ala | His | Val | Thr | Lys | Arg | Ser | Ile | Ala | Asp | Val | Ala | Ala | Ser | Gly |
|     |     |     |     | 350 |     |     |     |     | 355 |     |     |     | 360 |     |
| Pro | Gly | Leu | Ala | Phe | Leu | Ala | Tyr | Pro | Glu | Ala | Val | Thr | Gln | Leu |
|     |     |     |     | 365 |     |     |     |     | 370 |     |     |     | 375 |     |
| Pro | Ile | Ser | Pro | Leu | Trp | Ala | Ile | Leu | Phe | Phe | Ser | Met | Leu | Leu |
|     |     |     |     | 380 |     |     |     |     | 385 |     |     |     | 390 |     |
| Met | Leu | Gly | Ile | Asp | Ser | Gln | Phe | Cys | Thr | Val | Glu | Gly | Phe | Ile |
|     |     |     |     | 395 |     |     |     |     | 400 |     |     |     | 405 |     |
| Thr | Ala | Leu | Val | Asp | Glu | Tyr | Pro | Arg | Leu | Leu | Arg | Asn | Arg | Arg |
|     |     |     |     | 410 |     |     |     |     | 415 |     |     |     | 420 |     |
| Glu | Leu | Phe | Ile | Ala | Ala | Val | Cys | Ile | Ile | Ser | Tyr | Leu | Ile | Gly |
|     |     |     |     | 425 |     |     |     |     | 430 |     |     |     | 435 |     |
| Leu | Ser | Asn | Ile | Thr | Gln | Gly | Gly | Ile | Tyr | Val | Phe | Lys | Leu | Phe |
|     |     |     |     | 440 |     |     |     |     | 445 |     |     |     | 450 |     |
| Asp | Tyr | Tyr | Ser | Ala | Ser | Gly | Met | Ser | Leu | Leu | Phe | Leu | Val | Phe |
|     |     |     |     | 455 |     |     |     |     | 460 |     |     |     | 465 |     |
| Phe | Glu | Cys | Val | Ser | Ile | Ser | Trp | Phe | Tyr | Gly | Val | Asn | Arg | Phe |
|     |     |     |     | 470 |     |     |     |     | 475 |     |     |     | 480 |     |
| Tyr | Asp | Asn | Ile | Gln | Glu | Met | Val | Gly | Ser | Arg | Pro | Cys | Ile | Trp |
|     |     |     |     | 485 |     |     |     |     | 490 |     |     |     | 495 |     |
| Trp | Lys | Leu | Cys | Trp | Ser | Phe | Phe | Thr | Pro | Ile | Ile | Val | Ala | Gly |
|     |     |     |     | 500 |     |     |     |     | 505 |     |     |     | 510 |     |
| Val | Phe | Ile | Phe | Ser | Ala | Val | Gln | Met | Thr | Pro | Leu | Thr | Met | Gly |
|     |     |     |     | 515 |     |     |     |     | 520 |     |     |     | 525 |     |
| Asn | Tyr | Val | Phe | Pro | Lys | Trp | Gly | Gln | Gly | Val | Gly | Trp | Leu | Met |
|     |     |     |     | 530 |     |     |     |     | 535 |     |     |     | 540 |     |
| Ala | Leu | Ser | Ser | Met | Val | Leu | Ile | Pro | Gly | Tyr | Met | Ala | Tyr | Met |
|     |     |     |     | 545 |     |     |     |     | 550 |     |     |     | 555 |     |
| Phe | Leu | Ala | Leu | Lys | Gly | Ser | Leu | Lys | Gln | Arg | Ile | Gln | Val | Met |
|     |     |     |     | 560 |     |     |     |     | 565 |     |     |     | 570 |     |
| Val | Gln | Pro | Ser | Glu | Asp | Thr | Val | Arg | Pro | Glu | Asn | Gly | Pro | Glu |
|     |     |     |     | 575 |     |     |     |     | 580 |     |     |     | 585 |     |
| His | Ala | Gln | Ala | Gly | Ser | Ser | Thr | Ser | Lys | Glu | Ala | Tyr | Ile |     |
|     |     |     |     | 590 |     |     |     |     | 595 |     |     |     |     |     |

( 2 ) INFORMATION FOR SEQ ID NO:6:

( i ) SEQUENCE CHARACTERISTICS:
( A ) LENGTH: 40 base pairs
( B ) TYPE: nucleic acid
( C ) STRANDEDNESS: double
( D ) TOPOLOGY: linear ( i i ) MOLECULE TYPE: DNA ( i i i ) HYPOTHETICAL: YES ( i v ) ANTI-SENSE: NO ( i x ) FEATURE:
            ( A ) NAME/KEY: -
            ( B ) LOCATION: 1..40
            ( D ) OTHER INFORMATION: /label=consensus
                    / note= "consensus sequence of VNTR element in 3'
                    untranslated region of HUDAT cDNA"

( x i ) SEQUENCE DESCRIPTION: SEQ ID NO:6:

AGGAGCGTGT ACTATCCCAG GACGCATGCA GGGCCCCCAC          40

( 2 ) INFORMATION FOR SEQ ID NO:7:

( i ) SEQUENCE CHARACTERISTICS:
            ( A ) LENGTH: 23 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "oligonucleotide primer
                    T3-5LONG, upstream primer for PCR analysis of VNTR
                    region in 3'untranslated portion of HUDAT gene"

( i i i ) HYPOTHETICAL: NO ( i v ) ANTI-SENSE: NO ( x i ) SEQUENCE DESCRIPTION: SEQ ID NO:7:

TGTGGTGTAG GGAACGGCCT GAG          23

( 2 ) INFORMATION FOR SEQ ID NO:8:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "oligonucleotide primer
                    T7-3aLONG; downstream primer for PCR analysis of VNTR
                    region in HUDAT gene"

( i i i ) HYPOTHETICAL: NO ( i v ) ANTI-SENSE: YES ( x i ) SEQUENCE DESCRIPTION: SEQ ID NO:8:

CTTCCTGGAG GTCACGGCTC AAGG          24

( 2 ) INFORMATION FOR SEQ ID NO:9:

( i ) SEQUENCE CHARACTERISTICS:
            ( A ) LENGTH: 11 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "oligonucleotide adapter"

( x i ) SEQUENCE DESCRIPTION: SEQ ID NO:9:

GGGTCTAGAC G          11

( 2 ) INFORMATION FOR SEQ ID NO:10:

-continued

```
( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "oligonucleotide adapter"

( x i ) SEQUENCE DESCRIPTION: SEQ ID NO:10:

AATTCGTCTA GACCC                                                        15
```

SEQUENCE OF HUMAN DOPAMINE TRANSPORTER CDNA

RELATED APPLICATIONS

This application is a continuation of application Ser. No. 07/889,723 filed on Jun. 1, 1992, now abandoned, which is a continuation-in-part of application Ser. No. 07/762,132 filed on Sep. 20, 1991, U.S. Pat. No. 5,312,734.

BACKGROUND OF THE INVENTION

1. Field of the Invention

The invention relates to a cloned CDNA which encodes the human dopamine transporter protein. The cloned cDNA provides a means of expressing human dopamine transorter protein in a variety of contexts and also provides a means of diagnosing and treating diseases presenting abnormal expression of dopamine transporter protein.

2. Description of the Related Art

Throughout this application, reference is made to articles of the scientific literature and the like. The entire content of such citations is hereby incorporated by such reference.

The dopamine transporter that acts to take released dopamine back up into presynaptic terminals has been implicated in several human disorders. Cocaine binds to the dopamine transporter and blocks dopamine reuptake in a fashion that correlates well with cocaine reward and reinforcement (M. C. Ritz et al., Science 237, 1219 (1987)). Neurotoxins that cause Parkinsonian syndromes are concentrated in dopaminergic neurons by this transporter (S. H. Snyder and R. J. D'Amato, Neurology 36, 250 (1986); G. Uhl, Eur. J. Neurol. 30, 21 (1990)). Binding to the dopamine transporter is altered in brains of patients with Tourette's syndrome (H. S. Singer et al., Ann. Neurol. 30, 558 (1991)). These clinical links enhance interest in the structure and function of the human dopamine transporter (HUDAT). Vulnerability to these disorders may have genetic components (E. J. Devor and C. R. Cloninger, Annu. Rev. Genet. 23, 19 (1989); D. Pauls and J. Leckman, New Eng. J. Med. 315, 993 (1986); R. Pickens et al., Arch. Gen. Psychiatry 48, 19 (1991)); thus identification of linkage markers for the human DAT is also of interest.

Dopamine transporters act to terminate dopaminergic neurotransmission by sodium- and chloride-dependent reaccumulation of dopamine into pre-synaptic neurons (L. L. Iversen, in Handbook of Psychopharmacology, L. L. Iversen, S. J. Iversen, & S. H. Snyder, Eds. (Plenum, New York, 1976), pp. 381–442; M. J. Kuhar and M. A. Zarbin, J. Neurochem. 31, 251 (1978); A. S. Horn, Prog. Neurobiol. 34, 387 (1990)).

Cocaine and related drugs bind to these transporters in a fashion that correlates well with their behavioral reinforcing and psychomotor stimulant properties; these transporters are thus the principal brain "cocaine receptors" related to drug abuse (M. C. Ritz, R. J. Lamb, S. R. Goldberg, M. J. Kuhar, Science 237,1219 (1987); J. Bergman, B. K. Madras, S. E. Johnson, R. O. Spealman, J. Pharmacol. Exp. Ther. 251, 150 (1989).). The transporters accumulate neurotoxins with structural features resembling dopamine; their ability to concentrate the parkinsonism-inducing toxin MPP+ (1-methyl-4-phenylpyridinium) is key to this agent's selective dopaminergic neurotoxicity (S. H. Snyder, and R. J. D'Amato, Neurology 36(2), 250 (1986); S. B. Ross, Trend. Pharmacol. Sci. 8, 227 (1987)). Studies of the dopamine transporter protein suggest that it is an 80 kDa glycoprotein, but have not yet yielded protein sequence data (D. E. Grigoriadis, A. A. Wilson, R. Lew, J. S. Sharkey & M. J. Kuhar, J. Neurosci. 9, 2664 (1989)). Binding of cocaine analogs such as [$^3$H]CFT to membranes prepared from dopamine-rich brain regions reveals two sites with differing affinities (F. Javory-Agid, and S. Z. Langer, Naunyn-Schmiedeberg's Arch. Pharmacol. 329, 227 (1985); J. W. Boja, and M. J. Kuhar, Eur. J. Pharmacol. 173, 215 (1989); B. K. Madras et al., Mol. Pharmacol. 36, 518 (1989); M. J. Kuhar et al., Eur. J. Neurol. 30(1), 15 (1990); M. C. Ritz, E. J. Cone, M. J. Kuhar, Life Sci. 46, 635 (1990); D. O. Calligaro, and M. E. Eldefrawi, J. Pharmacol. Exp. Ther. 243, 61 (1987); B. K. Madras et al., J. Pharmacol. Exp. Ther. 251(1), 131 (1989); M. C. Ritz et al., J. Neurochem. 55, 1556 (1990)).

Recent elucidation of cDNAs encoding dopamine transporters from experimental animals (B. Gros et al., FEBS Lett. 295, 149 (1992); J. E. Kilty et al., Science 254, 578 (1991); S. Shimada et al., Science 254, 576 (1991); T. B. Usdin et al., Proc. Natl. Acad. Sci. U.S.A. 88, 11168 (1991) provides hybridization probes useful for isolation of their human cognate.

SUMMARY OF THE INVENTION

Described herein is a cDNA (pcHUDAT), which encodes the human dopamine transporter protein (HUDAT). Also described are unique features of the nucleotide sequence of the pcHUDAT predicted for its encoded mRNA and protein, restriction fragment length polymorphisms (RFLPs) and Variable Number Tandem Repeats (VNTRs) identified by this CDNA and estimates of race-specific population frequencies of these RFLPs and VNTRs.

By virtue of its representation of the human dopamine transporter sequence, the pcHUDAT is advantageous over those clones isolated from other species in that better results in applications having a human context would be expected.

The CDNA encoding the human dopamine transporter protein (HUDAT) provides a means for diagnosing and treating disorders that arise by expression of abnormal amounts of or dysfunctional dopamine transporter molecules in a human being.

It is one object of the invention to produce a cDNA that encodes the human dopamine transporter protein, a product of dopaminergic neurons that binds dopamine, cocaine and cocaine analogs and will transport dopamine and MPP+ into mammalian cells expressing it on their surface.

It is a further object of the invention to utilize the cDNA to produce cell lines that express human DAT on their surface and to provide a method for the screening of compounds that influence the binding and/or transport of dopamine or cocaine or functional analogs thereof to (into) the cells. Compounds which demonstrate displacement of [$^3$H]-labelled CFT binding from expressed DAT and/or striatal membrane preparations are considered "functionally equivalent cocaine analogs". Such cell lines may also find therapeutic application for treatment of diseases caused by depletion of cell populations which normally provide for uptake of dopamine.

A third object of the invention is to provide diagnostic means for assessing HUDAT expression in patients by DNA- or antibody-based tests and for assessing the onset or progression of disease by assay of HUDAT degradation.

These and other objects are accomplished by providing a cDNA encoding the dopamine transporter protein and a purified polypeptide conferring upon cells the phenotype of dopamine uptake from the surrounding extracellular medium. Further, the invention is embodied in cell lines, created by stable transformation of cells by a vector encoding the dopamine transporter protein, expressing the dopamine transporter protein on their surface. Another aspect of the invention relates to a method of using such lines to screen pharmaceutical compositions for their ability to inhibit the binding of dopamine, cocaine or analogs of these compounds to the transporter protein. Such a screening can also be accomplished by use of cells transiently expressing dopamine transporter cDNA. The invention also relates to diagnostic applications of the dopamine transporter cDNA and anti-human DAT antibodies and to therapeutic applications of the HUDAT cDNA.

BRIEF DESCRIPTION OF THE DRAWINGS

FIG. 1 (SEQ. ID. NO. 1) shows the nucleotide sequence of the pcHUDAT cDNA encoding the human dopamine transporter protein; the sequence is a composite derived from the sequence of clones pHCDAT2, pHCDAT3 and pHCDAT7.

FIG. 2 shows the sequences of the repeat elements in the 3' untranslated portion of the pcHUDAT cDNA (residues 2724 to 3117 of SEQ. ID. NO.:1). Also shown is the consensus sequence of the repeats (SEQ. ID. NO.:6).

FIG. 3 shows a comparison of the amino acid sequence of the human dopamine transporter (Hdat, SEQ. ID. NO.:2) protein with the amino acid sequence of the rat DAT (Dat1, SEQ. ID. NO.:4) and also with the sequences of the human norepinephrine transporter (Hnat, SEQ. ID. NO.:3) and of the human gamma-amino-butyric acid transporter (Hgabat, SEQ. ID. NO.:5).

DETAILED DESCRIPTION OF THE INVENTION

Figure 4A:
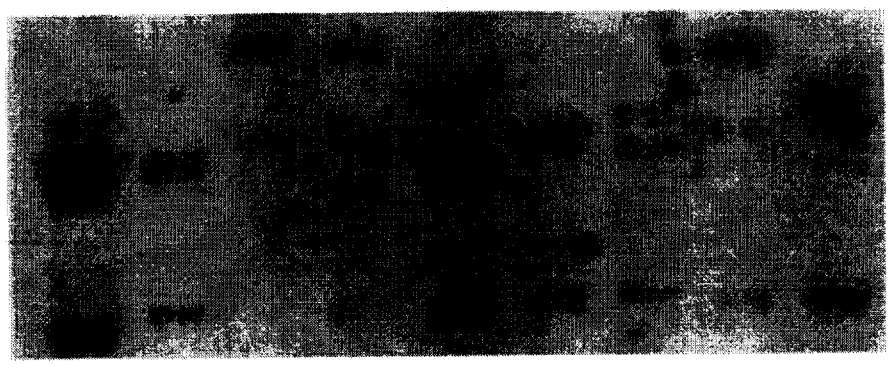
FIG. 4A shows a representative RFLP analysis of human genomic DNA from nine unrelated individuals digested with TaqI and hybridized with the insert portion of the pHCDAT7 plasmid.

For many of the applications described in the examples below subfragments or variants of the HUDAT protein disclosed in the present application wherein the original amino acid sequence is modified or changed by insertion, addition, substitution, inversion or deletion of one or more amino acids are useful so far as they retain the essential binding or transport specificity for dopamine, cocaine, or functional analogs thereof. Thus, such variants of the HUDAT are considered to fall within the scope of the present invention. Such variants are easily produced by mutagenic techniques well developed in the art of genetic engineering.

Expression of heterologous proteins in *E. coli* is often utilized as a means of obtaining large quantities of a polypeptide. The product is an unglycosylated protein, which may be made as insoluble "inclusion bodies" in the bacterial cells. Alternatively, some proteins can be secreted into the perplasmic space by fusion to a leader sequence that directs the secretion of the translation product. Other useful fusion sequences are those which allow affinity purification of the product, such as the pGEX system (Pharmacia), which allows purification by use of a glutathione-Sepharose column.

The promoter to be employed is dependent upon the particular protein to be expressed. Some proteins are not detrimental to the physiology of the bacteria and may be expressed using a high-level constitutive promoter. Others are somewhat toxic and so are best expressed from an inducible promoter which keeps synthesis of the heterologous protein repressed until growth of the culture is complete. The promoter is then switched on and the heterologous protein is produced at a high level.

Other considerations in bacterial expression include the use of terminator seqences in the transcription unit and the use of sequences in the 5'-untranslated portion of the MRNA to abolish secondary structure which might impede translation. Also the choice of bacterial strain can be important. Some heterologous proteins are susceptible to proteolytic degradation and so are best expressed in strains of bacteria which lack proteolytic functions. Also, strains of bacteria other than *E. coli* are often useful as hosts for expression systems. The best-developed alternative currently being Bacillus strains.

Expression of proteins in bacteria is well-reviewed in "Current Protocols in Molecular Biology", which is published with quarterly updates by Wiley Interscience.

Expression of "foreign" proteins in mammalian cells can be accomplished in two general fashions. Transient expression refers to the creation of a pool of transfected cells which harbor plasmids that are not stably maintained in the cell and so are gradually diluted out of the population. Transient expression is by nature a short term method. For reproducible expression of a heterologous protein, stable expression systems are preferable. The current state of this art includes a variety of vector systems; both integrative and autonomous vectors are available. Inducible expression of heterologous proteins in mammalian cells is difficult to achieve at the current time. Some systems have been described, but they are not yet in general use. More commonly used are vectors bearing moderate to high-level constitutive promoters. Plasmid vectors are relatively easy to use. Retroviral vectors, which rely upon packaging into infective viral particles and integration into the host cell chromosome are more difficult to use, due to the extra steps involved in creating the recombinant viruses and cell lines which secrete them, but have the advantage that they effectively introduce exogenous DNA into human cell lines. Vaccinia virus vector systems are also in widespread use. Other viral vectors are under development for gene therapy systems, including adenovirus-derived vectors.

The preferred embodiments of the invention are described by means of the following examples. These examples are intended to be illustrative, rather than limiting in scope. It is understood that variations in the materials and techniques described below will be apparent to those skilled in art and such are to be considered to fall within the scope and spirit of the instant application.

EXAMPLE 1

Isolation and sequencing of cDNA encoding human dopamine transporter

To isolate human cDNAs for the dopamine transporter, CDNA libraries prepared from "substantia nigra" and "brainstem" dissections containing cells known to express the transporter were screened with hybridization probes prepared from the rat cDNA, pDAT1 (S. Shimada et al., Science 254, 576 (1991)). Sequences from the 3' untranslated region of the rat cDNA were not used because of the presence of CA dinucleotide repeats. Human brain stem and substantia nigra cDNA libraries (Stratagene, La Jolla, Calif.) were plated and blotted onto duplicate replica nitrocellulose (Schleicher and Schuell, Keene, N.H.) filters, which were incubated for 1 hour at 37° C. with proteinase K (50 µg/µl in 2×SSPE/0.1% SDS) to reduce filter background, washed in 5×SSC/0.5% SDS/1 mM EDTA, prehybridized and hybridized at 42° C., and washed at 54° C. in 0.4×SSC/0.5% SDS. The hybridization probe was a 2300 bp Eco RI fragment of the rat dopamine transporter cDNA6 (S. Shimada et al., Science 254, 576 (1991)) [$^{32}$P] labeled by random priming (Prime It kit, Boehringer Mannheim), and hybridized at approximately $10^6$ cpm/ml. Positively-hybridizing cDNA clones were purified from the brainstem library, autoexcized according to protocols provided by the manufacturer (Stratagene), and termed pHCDAT2, pHCDAT3, and pHCDAT7. Sequencing was performed on an Applied Biosystems automated sequencer as described (S. Shimada et al., Science 254, 576 (1991)). Sequence analysis was performed using the GCG software package (J. Devereaux, et al., Nucleic Acids Res. 12, 387 (1984)).

Screening of more than $2\times10^6$ plaques from the substantia nigra library produced no positives. Screening $1\times10^6$ plaques from the brainstem library yielded 11 positively-hybridizing plaques, three of which were identified as human DAT clones by sequence analysis. These clones were identified as representing the 5'-half (pHCDAT2, bases 1–1733), the 3'-half (pHCDAT3, bases 1679–3919), and an internal portion (pHCDAT7, bases 653–1434) of the human DAT cDNA whose reconstructed full-length sequence is shown in FIG. 1. The structure of this CDNA resembles the structure of the rat CDNA DAT1, with a modest 5' untranslated region and a long 3' untranslated region. Both 5' and 3' untranslated regions are longer than those of the rat cDNA pDAT1, however, making the length of the predicted human mRNA greater than the 3.7 kb observed for the rat mRNA (S. Shimada et al., Science 254, 576 (1991)). A striking difference between rat and human cDNAs is found in the 3' untranslated region where the human cDNA displays 10 copies of a 40 bp repetitive element that are arrayed in head-to-tail fashion and are absent from the rat CDNA (FIGS. 1,2). These elements are highly stereotyped. The sequence of each element is more than 90% identical to the consensus sequence listed at the bottom of FIG. 2, although the seventh repeat displays a 5 base pair insertion from its 24th to 28th nucleotides. The consensus element found here is 68% G+C. No exact match is found in searches of the EMBL/genbank data base, release 70. However, sequences conferring up to 70% nucleic acid identity over up to 37 of these bases are found in viral sequences, especially with herpesvirus sequences (e.g. locus HS1US).

The open reading frame predicted by the HUDAT cDNA encodes 620 amino acids, identical in size to the rat DAT1 cDNA except for an additional amino acid (199) not found in the rat sequence (FIG. 3) This open reading frame predicts amino acid sequences that are 94% identical to those encoded by the rat dopamine transporter cDNA (S. Shimada et al., Science 254, 576 (1991)). This high degree of conservation, and the weaker identities with the human norepinephrine and GABA transporter cDNA (H. Nelson et al., FEBS Lett. 269, 181–184 (1990); T. Pacholczyk et al., Nature 350, 350–354 (1991)) (FIG. 3), identifies this as the human homolog of the rat DAT1.

The amino acid sequence predicted by the HUDAT cDNA reveals interesting differences from the rat cDNA. It lacks one of the 4 consensus sites for N-linked glycosylation noted in the rat DATI CDNA (FIG. 3, + symbol). Three adjacent amino acids distinguish the human from the rat proteins at this locus; no other portion of the molecule differs by this extent.

Human DAT amino acids predicted to lie within hydrophobic, putative transmembrane domains show 97% amino acid identity between the rat and human transporter cDNAs. This conservation is higher than the 87% conservation in regions thought not to span the membrane, and is consistent with the high conservation in these regions among different sodium dependent transporter family members. The most striking difference between the rat and human transporters occurs in the putative second extracellular domain, at which each of the transporters cloned to date displays consensus sites for N-linked glycosylation. The glycosylation of the rat dopamine transporter has been defined in biochemical studies that suggest 20 to 30 kd of the molecular weight of the mature protein may consist of sugar (R. Lew et al., Brain Research 539, 239 (1991). Four potential N-linked glycosylation sites indicated in the rat transporter contain classic asparagine-X-serine/threonine sequences. Three of these sites are conserved among the rat and human sequences, but a middle glycosylation site, potentially the most distant from the embedding membrane, is absent in the human transporter. The amino acids surrounding this site provide the largest area of amino acid sequence divergence between the rat and human transporters. If glycosylation is evenly distributed among the different potential sites for N-linked glycosylation, these observations would predict that the human dopamine transporter might display less glycosylation than the rat, and that its molecular weight might be correspondingly smaller. The function of the glycosylation has not been identified to date; changes in ligand recognition, membrane targeting of the molecule, or even in cell/cell recognition might conceivably result from these differences in glycosylation.

The repeated motifs in the 3' untranslated regions of these cDNAs are another interesting difference from the rat sequence. Smaller polymorphic repeated elements have gained recent attention due to their implication in the fragile X syndrome and myotonic dystrophy (J. D. Brook, et al., Cell 68, 799–808 (1992); Y. Fu et al., Cell 67, 1047–1058 (1991); V. A. McKusick, Mendelian Inheritance in Man, 9th edn., Johns Hopkins University Press, Baltimore, 1990, 2028 p.). The rat sequence does demonstrate 25 copies of a small dinucleotide CA repeat from bases 2476 to 2525 of the 3' untranslated region of its mRNA; CA repeats are absent from the human cDNA (S. Shimada et al., Science 254, 576–578 (1991)). The sequence of the longer hDAT repeated element is not found the rat CDNA, nor in searches of other sequences found in databanks. The significance of the partial matches in viral genomes is unclear. These repeated elements might alter mRNA properties, perhaps including secondary structure and/or half-life, in ways that could contribute to the regulation of this gene's expression. Search of this sequence using the stemloop program yields more than 150 possible loops with as many as 18 stabilizing hydrogen bonds. Conceivably, population variants in the number of these repeats could also contribute to heterogeneity in DAT function.

EXAMPLE 2

Restriction Fragment Length Polymorphism (RFLP) analysis

DNA was obtained from leukocytes, digested with TaqI, and analyzed by Southern blotting using pHCDAT7 as the initial hybridization probe. Simpler patterns were also obtained using two other hybridization probes. Taq 120 corresponds to bases 668 to 787 of the HDAT (see below), and was generated by hybridizing 65 and 72 base oligonucleotides of opposite sense and extending the product using large fragment of DNA polymerase I and [$^{32}$P]-dCTP or by random priming of these two hybridized oligonucleotides, as described (A. Feinberg and B.

Vogelstein, Analyt. Biochem. 132, 6–9 (1982); S. Shimada et al., Science 254, 576–578 (1991)). Identical results were also obtained using a random-priming labeled 492 base pair cDNA fragment (Taq 492) corresponding to bases 301 to 793 of this sequence. Probes were hybridized to filters containing DNA from unrelated individuals at 42° C. in hybridization solution containing 50% formamide as described. Identical results were obtained with final washes at 68° C. in 0.2×SSC/0.2% SDS or at 54° C. in 0.4×SSC/0.5% SDS. Patterns from these Southern blots were analyzed by two independent observers.

Figure 4B:
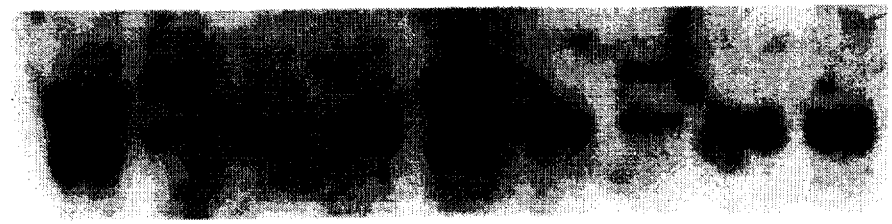
FIG. 4B shows the same DNA, but hybridized with the Taq492 probe, which corresponds to nucleotides 301–793 of the pcHUDAT sequence.

Digestion of DNA from 20 unrelated individuals with nine different restriction endonucleases revealed Southern blot patterns in each case that were consistent with the presence of a single gene. There were no clear interindividual differences in Southern blot restriction patterns using radiolabeled PHCDAT 7 after digestion with Alu I, Bam HI, Eco RI, Hae III, Hind III, Msp I, and Rsa I. Three other enzymes, Pst I, Hinf I and Taq I revealed polymorphisms. We focused on the polymorphisms identified by Taq I. When probed with radiolabeled PHCDAT 7, more than six bands were obtained from Taq I restricted DNA, many of which showed polymorphic patterns (FIG. 4A) Hybridization survived washes of up to 68° C., consistent with specificity. A simpler pattern was revealed when hybridization was performed with the Taq 120 hybridization probe or with the cDNA hybridization probe Taq 492 (FIG. 4B). Two hybridizing bands of 7 and 5.6 kilobases were observed and termed A1 and A2. Taq I A1 and A2 RFLP frequencies are presented the Table. Of 272 chromosomes from 136 individuals examined 36% showed the A1 form, 64% showed the A2 form. There was a significant racial dimorphism in these distributions such that 26% of Caucasians, but 42% of blacks displayed the A1 RFLP ($\chi^2$=7.45, p<0.01).

The rich patterns of Taq I RFLPs identified with this cDNA sequence could relate to the fact that the clone itself contains three sites for Taq I cleavage. Further studies are thus likely to detect other polymorphisms, because extreme variability of bands in the initial Taq I restriction digestions has already been documented.

The tandem repeat in the 3'region of this gene also provides a Variable Number Tandem Repeat (VNTR). The means for examining the distribution of alleles of the VNTR is set forth at the end of Example 3 below.

The hybridization probes that we have described provide useful markers for linkage analysis that would help to exclude the regions around the dopamine transporter gene from involvement in familial disorders. Human dopamine systems are involved in a number of human disorders, with specific implication of involvement of transporter mechanisms in psychostimulant abuse, Parkinsonism, and Tourette's syndrome (E. J. Devor and C. R. Cloninger, Annu. Rev. Genet. 23, 19–36 (1989); D. Pauls and J. Leckman, New Eng. J. Med. 315, 993–997 (1986); R. Pickens et al., Arch. Gen. Psychiatry 48, 19–28 (1991); M. C. Ritz et al., Science 237, 1219–1223 (1987); S. Shimada et al., Science 254, 576–578 (1991); H. S. Singer et al., Ann. Neurol. 30, 558–562 (1991); S. H. Snyder S. H. and R. J. D'Amato, Neurology 36, 250–258 (1986); G. Uhl, Eur. J. Neurol. 30, 21–30 (1990)). The human dopamine transporter cDNAs and RFLP information described here should provide useful tools to study its possible role in these and other human disorders.

EXAMPLE 3
(Predictive)

A genetic component of substance abuse behavior identified by RFLP analysis of the human DAT gene Abuse of substances, including drugs and alcohol, is currently viewed as arising from a combination of biological, psychological, and social factors (J. S. Searles, J. Abnorm Psychol. 97,153–167 (1988); E. J. Devor and C. R. Cloninger, Annu Rev Genet. 23, 19–36 (1989); K. R. Merikangas, Psychological Medicine 20, 11–22 (1990)). Genetic contributions to susceptibility to alcoholism are supported by family, twin, and adoption studies. (D. S. Goodwin, Arch Gen Psychiatry 36, 57–61 (1979); C. R. Cloninger et al., Arch Gen Psychiatry 38, 861–868 (1981); C. R. Cloninger, Science 236, 410–416 (1987)). A genetic component of vulnerability to drug abuse has also been suggested in both twin and adoption studies (R. J. Cadoret et al., Arch Gen Psychiatry 43, 1131–1136 (1987); R. W. Pickens et al., Arch Gen Psychiatry 48, 19–28 (1991)).

A number of substances which share the potential for abuse by humans also share the ability to enhance dopamine activity in mesolimbic/mesocortical circuits thought to be important for behavioral reward and reinforcement (A. S. Lippa et al., Pharmacol Biochem Behav. 1, 23–28 (1973); G. Di Chiara and A. Imperato, Proc Natl Acad Sci U.S.A. 85, 5274–5278 (1988); R. A. Wise and P. P. Rompre, Annu Rev Psychol. 40, 191–225 (1989)). Cocaine's ability to inhibit re-uptake of dopamine, for example, points strongly toward a possible direct action for this highly-reinforcing drug in these dopaminergic circuits (M. C. Ritz et al., Science 237, 1219–1223 (1987); D. E. Grigoriadis et al., J. Neurosci. 9, 2664–2670 (1989)).

Blum, Noble and co-workers first reported that the "A1" TaqI restriction fragment length polymorphism (RFLP) of the human dopamine $D_2$ receptor gene (DRD2, D. K. Grandy et al., Am J. Hum Genet. 45, 778–785 (1989)) was associated with alcoholism (K. Blum et al., JAMA 263, 2055–2060 (1990)); 69% of alcoholics displayed this RFLP compared to 20% of non-alcoholics. 42% of 504 Caucasian alcoholic individuals reported in literature to date display this RFLP, while only 27% of 461 Caucasian "control" individuals are A1 positive (G. R. Uhl et al., Arch Gen Psychiatry 49, 157–160 (1992); E. Turner et al., Biol Psychiatry 31, 285–290 (1991). These data come from eight previous studies, five of which find significant associations between RFLP and alcoholism, and provide evidence for a significant association between gene markers and behavior.

Examination of gene marker/behavior associations in drug abusers raises several methodological concerns. Relatively few individuals who abuse drugs abstain from alcohol, and many individuals who use drugs often self-administer multiple substances (D. R. Wesson et al., eds. *Polydrug Abuse: The Results of a National Collaborative Study*. New York, N.Y.: Academic Press, Inc.; 1978). Drug-using populations may also differ from one another and from the general population in racial, ethnic and other features that might be associated with altered distributions of the alleles for different genes (M. R. Gillmore et al., Am J Drug Alcohol Abuse 16, 185–206 (1990)). Also, some clinical assessments may not focus on the heritable features of the disorder (R. W. Pickens et al., Arch Gen Psychiatry 48, 19–28 (1991)).

A study of $D_2$ dopamine receptor gene markers in polysubstance users and control subjects provides a useful model for investigating the association between alleles of the DAT gene and substance abuse behaviors or other behavioral disorders such as Tourette's syndrome. We have investigated the 3' TaqI A1 RFLP examined in previous studies of alcoholics, and a more 5' TaqI RFLP ("B") located closer to regulatory and structural/coding regions of the gene (X. Y. Hauge et al., Genomics 10, 527–530 (1991)). Only Caucasian individuals were included in this study because of evidence for different distributions of TaqI A and B markers in white and black individuals (Dr Bruce O'Hara et al, unpublished data). Substance users were identified according to two approaches. One group of users met criteria for lifetime DSM-III-R (*Diagnostic and Statistical Manual of Mental Disorders*, Revised Third Edition. Washington, D.C.: American Psychiatric Association; 1987) psychoactive substance use disorder(s). A second group of users was identified based on their peak lifetime use of psychoactive substances. This quantity-frequency approach was chosen because of evidence that heavy use of alcohol may display significant heritability in males and females (R. W. Pickens et al., Arch Gen Psychiatry 48, 19–28 (1991)). Control subjects were free of significant lifetime substance use.

i) Subject Recruitment: 288 Caucasian substance-using and control subjects were recruited from three sources; 21% were female. 224 drug-using and control volunteers consenting to research protocols at the Addiction Research Center (ARC) in Baltimore, Md. were studied. The ARC is the major federal drug abuse research facility that recruits through advertisement and word of mouth for participation in treatment and non-treatment studies. 12 volunteers from a chronic hemodialysis unit on the same campus, both users and controls, augmented this sample. A third group of users consisted of 52 HIV seronegative participants in an ongoing east Baltimore study of HIV infections in intravenous drug users (D. Vlahov et al., Am J Epid. 132, 847–856 (1990)).

Each subject was individually interviewed to elicit information characterizing substance use. 192 users and 56 controls were assessed according to a quantity-frequency approach. 137 users met criteria for DSM-III-R psychoactive substance use disorders. 97 users received both assessments. Written informed consent was obtained from all subjects.

Quantity-Frequency Approach: Trained interviewers assessed subjects with the Drug Use Survey (DUS) interview (see below) in a confidential setting. The amount, frequency, and/or dollar cost at the time of lifetime peak use were recorded for each of 15 different psychoactive drugs or drug classes used more than five times. Blinded ratings of lifetime peak use of each individual substance were made on a four-point scale: 0=absent, 1=minimal, 2=moderate, or 3=heavy use as indicated in Table I. A composite "Total Use" index was constructed from the pooled ratings of use of all individual substances as follows: "0"=up to minimal use of alcohol, marijuana, or nicotine and no use of other drugs; "1"=moderate use of alcohol or nicotine and/or minimal use of other drugs; "2"=heavy use of alcohol or nicotine, moderate use of marijuana, and/or up to moderate use of other drugs; "3"=heavy use of any illicit drug. Thus, neither heavy use of alcohol or nicotine was sufficient to confer a rating of heavy total drug use. Control subjects were identified as those individuals with Total Use scores of 0 or 1; substance abusers were individuals with Total Use scores of 2 or 3.

DSM-III-R Diagnoses: Trained interviewers administered the Diagnostic Interview Schedule Version III Revised (DIS-III-R, L. N. Robins et al., *NIMH Diagnostic Interview Schedule Version III* Revised (Version Nov. 7, 1989). Department of Psychiatry, Washington University School of Medicine, St. Louis, Mo.) to provide lifetime DSM-III-R diagnoses of psychoactive substance use disorders including nicotine and alcohol.

Reliability and Validity of Drug Use Information: Drug Use Survey (DUS) ratings were evaluated in subjects who were: (a) assessed with the DUS on two different occasions at 3 to 13 months apart (n=31), (b) tested for lifetime DSM-III-R psychoactive substance use disorders by the DIS-III-R[23] (n=18) and the Structured Clinical Interview for DSM-III-R (R. L. Spitzer et al., Structured clinical interview for DSM-III-R-patient version (with psychotic screen)-SCID-P (W/Psychotic Screen)—May 1, 1989). Biometrics Research Department, New York State Psychiatric Institute, New York, N.Y.)(SCID; n=17), and (c) checked for urinary excretion of psychoactive drugs and metabolites on the day of the DUS (n=56). For the 18 DIS-III-R-assessed subjects and the 17 SCID-assessed subjects, DUS ratings were completed without knowledge of psychiatric assessment information. Genotypes were not available for 17 subjects assessed with the SCID and were not included in the genetic analyses.

TABLE I

Drug Use Survey - Rating Criteria

| Substance | |
|---|---|
| Cigarettes | 0 = never smoked cigarettes |
| | 1 = 1 to 15 cigarettes per day |
| | 2 = 16 to 25 cigarettes per day |
| | 3 = more than 25 cigarettes per day |
| Alcohol | 0 = never used alcohol |
| | 1 = up to 4 drinks per drinking occasion, fewer than 10 drinking occasions/month |
| | 2 = up to 4 drinks per drinking occasion, more than 10 drinking occasions/month, OR, more than 4 drinks per drinking occasion, but fewer than 10 drinking occasions/month |
| | 3 = 5 or more drinks per drinking occasion, more than 10 drinking occasions/month |
| Heroin; Other Opiates | 0 = never used heroin/other opiates illicitly |
| | 1 = used 1 time/week or less than $30/week |
| | 2 = 2 to 6 times/week, spending $30 to $100/day |
| | 3 = daily use, typically spending >$100/day |
| Cocaine | 0 = never used cocaine |
| | 1 = less than 2 grams per week (up to $150/week); typical use - about 1 gram per month |
| | 2 = 2 to 4 grams per week (more than $150/week but less than $300/week) |
| | 3 = more than 4 grams per week, usually up to 7 to 10 grams/week; (more than $300/week, usually much higher; daily use common) |
| Marijuana | 0 = never used marijuana |
| | 1 = up to one joint/day |
| | 2 = 2 to 3 joints per day |
| | 3 = 4 or more joints per day |
| Minor Tranquilizers, Amphetamines, Barbiturates, Hallucinogens, Inhalants, PCP, Antidepressants, Other Tobacco products, Other Substances | 0 = never used substance |
| | 1 = fewer than 1 use per week |
| | 2 = 1 to 6 uses per week (4 to 24 uses/month) |
| | 3 = 7 or more uses/week (more than 24 uses/month) | ii) DNA Extraction and Analysis: Blood was obtained in EDTA-containing evacuated sterile tubes from each subject and stored at 4° C. and/or frozen at −70° C. in polypropylene tubes. DNA was extracted from non-frozen samples after initial isolation of nuclei and from frozen blood by selective white blood cell sedimentation followed by standard extraction methods (J. Sambrook et al., eds. "Molecular cloning: a laboratory manual" (2nd edition). Cold Spring Harbor (New York) Laboratory Press; 1989). 5–10 µg of this DNA was digested with TaqI as recommended by the manufacturer, or with 20-fold excess of this enzyme for several individuals displaying A3 alleles. DNA fragments were electrophoresed using 0.8% agarose gels containing ethidium bromide at 1–2 volts per centimeter for 16 hours, transferred to nylon membranes, and immobilized by UV crosslinking.

Hybridization was performed for 16–24 hours at 42° C. in 50% formamide, 5×SSC, 50 mM NaPO$_4$ (pH 6.8), 1% SDS, 1 mM EDTA, 2.5×Denhardt's solution, 200 µg/ml herring sperm DNA, and 4×10$^6$ cpm/ml of radiolabelled DNA (see below). Washing for 20 minutes in 2×SSC at room temperature was followed by two 30 minute washes in 0.4×SSC/ 0.5% SDS at 55° C. Washed blots were exposed to Kodak XAR film 1–6 days with an intensifying screen at −70° C. Band sizes were compared to λ DNA molecular weight standards, and with patterns previously defined (K. Blum et al., JAMA 263, 2055–2060 (1990); A. M. Bolos et al., JAMA 264, 3156–3160 (1990). After TaqI A RFLP status was determined, $^{32}$P decay allowed rehybridization of the same blots with hybridization probe for TaqI B ascertainment. When background levels of radiation were not reached, filters were incubated at 65° C. for 30 min in 2 mM TRIS (pH 8), 1 mM EDTA, and 0.1% SDS to remove residual hybridized probe. RFLP status was assigned by two independent raters unaware of the clinical status of the subjects.

iii) Hybridization probes: A 1.7 kb BamHI fragment of the human genomic clone encoding the dopamine D$_2$ receptor (λhD2G1) was subcloned into the BamHI site on bluescript SK+to produce phD2-9, which was used to detect A1, A2, and A3 patterns in the Southern analyses, as described (K. Blum et al., JAMA 263, 2055–2060 (1990); A. M. Bolos et al., JAMA 264, 3156–3160 (1990)) (Dr Bruce O'Hara et al, unpublished data). λhD2G2 was used to detect the TaqI "B" patterns. DNAs were radiolabelled using random priming and $^{32}$P-CTP to specific activities of approximately 10$^9$ cpm/µg (A. Feinberg and B Vogelstein, Anal Biochem. 137, 266–267 (1984)).

iv) Analyses:
  a) Association analyses: A two-tailed Pearson chi square test (with Yates' correction for continuity) was used to evaluate the association between A1 RFLP presence and substance use/abuse; the same analysis were repeated for the B1 RFLP. Association was first tested contrasting controls and substance users meeting criteria for any lifetime DSM-III-R substance dependence disorder. Next, controls were contrasted with substance users who had been assessed with the DUS. Data for both groups of substance-using subjects were pooled and compared to RFLP frequencies for controls. b) Comparisons with other data: Pooled TaqI A1 RFLP data from ARC users was compared with values obtained for Caucasian controls in other studies. c) Subtracting heavy alcohol users: DUS-assessed users free of heavy alcohol use were compared with controls to test whether the associations observed might be attributed solely to alcohol.

TaqI A and B RFLPs were assigned with 100% agreement between two independent raters.

Substance use assessment by means of the Drug Use Survey showed several features suggesting validity and reliability. For 31 subjects whose DUS was elicited twice, interrater reliability correlations for severity ratings ranged from 0.83 to 1.00 (median=0.94), while test-retest reliability correlations for individual drugs ranged from 0.53 to 0.94 (median=0.78). For 35 subjects with DIS-III-R or SCID assessments and independent DUS ratings, analysis of the correspondence between a positive lifetime DSM-III-R Substance Use diagnosis and moderate to heavy substance use on the DUS yielded a kappa value of 0.68 (91% agreement). Finally, drugs tested as positive in urine drug screening were reported used 84% of the time (n=56) in the DUS assessment.

TaqI A and B RFLP frequencies for substance-using and control subjects are presented in Table II. For the TaqI B1 RFLP, a significant association was found comparing users with at least one lifetime DIS-III-R Substance Use Disorder diagnosis and DUS-assessed controls ($\chi^2$=6.74, p<0.01). For the TaqI A1 RFLP, analysis of the same groups revealed a significant association ($\chi^2$=3.98, p<0.05). Comparison of DUS-assessed users to DUS-assessed controls revealed a significant association for the TaqI B1 RFLP ($\chi^2$=5.45, p<0.02) and a trend towards significant association for the TaqI A1 RFLP ($\chi^2$=3.14, p<0.08). Table III presents TaqI A and B genotypes (homozygotes and heterozygotes) for DUS-assessed controls and users.

TABLE II

D$_2$ Dopamine Receptor Gene RFLPs in Users and Controls

| Group | A1 Present (%) | B1 Present (%) |
|---|---|---|
| I. POLYSUBSTANCE USERS | | |
| a) DSM-III-R Substance Use Diagnosis | 41.8 (51/122) | 34.4 (42/122) |
| b) DUS* Heavy Use (Total Use = 3) | 36.0 (45/125) | 29.6 (37/125) |
| c) DUS Moderate Use (Total Use = 2) | 44.8 (30/67) | 34.3 (23/67) |
| d) DUS Total Use 2 & 3 Combined | 40.8 (75/192) | 31.3 (60/192) |
| Combined Users @ | 41.4 (96/232) | 32.3 (75/232) |
| II. CONTROLS | | |
| a) DUS Minimal Use (Total Use = 1) | 30.0 (6/20) | 15.0 (3/20) |
| b) DUS Sparse Use (Total Use = 0) | 22.2 (8/36) | 13.9 (5/36) |
| Combined Controls | 25.0 (14/56) | 14.3 (8/56) |
| III. PREVIOUSLY REPORTED CONTROLS | | |
| a) Blum et al,[15] (1990)* | 16.7 (4/24) | |
| b) Blum et al,[36] (1991)* | 19.4 (6/31) | |
| c) Comings et al,[35] (1991)* | 15.0 (3/20) | |
| d) Parsian et al,[37] (1991)* | 12.0 (3/25) | |
| e) Todd et al,[+] (1991)* | 32.6 (15/46) | |
| f) Bolos et al,[26] (1990) | 33.9 (21/62) | |
| g) Comings et al,[35] (1991) | 23.9 (21/88) | |
| h) Gelernter et al,[38] (1991) | 35.3 (24/68) | |
| i) CEPH-Comings et al,[35] (1991) | 17.3 (9/52) | |
| j) Grandy et al,[14] (1989) | 37.2 (16/43) | |
| k) O'Hara et al,[++] (1992) | 29.7 (30/101) | |
| Subtotal | 27.1 (152/560 | |
| Combined Controls: | | |
| Prior and Current Reports    total | 26.9 (165/613) | |

DUS = Drug Use Survey
@The subject total here (n = 232 users) reflects 40 users who received only the DIS-III-R + 82 users who received the DIS-III-R and the DUS + 110 users who received only the DUS. Four subjects who received both the DIS-III-R and the DUS did not meet criteria for a DSM-III-R diagnosis but were classified as users (in the DUS and "Combined Users" comparisons) on the basis of their DUS ratings.
*Screened to exclude alcohol or drug abuse.
+Cited in Cloninger et al., JAMA 266, 1833 (1991).
++Unpublished data.

TABLE III

$D_2$ Dopamine Receptor Gene RFLP Frequencies in Users and Controls

| GENOTYPE | DUS Heavy Use (Total Use = 3) | DUS Moderate Use (Total Use = 2) | DUS Minimal Use (Total Use = 1) | DUS Sparse Use (Total Use = 0) |
|---|---|---|---|---|
| A1/A1 | 7/13[+] = .538 | 4/13 = .308 | 0/13 = .000 | 2/13 = .154 |
| A1/A2 | 38/76 = .500 | 26/76 = .342 | 6/76 = .079 | 6/76 = .079 |
| A2/A2 | 80/159 = .503 | 37/159 = .233 | 14/159 = .088 | 28/159 = .176 |
| B1/B1 | 3/9 = .333 | 4/9 = .444 | 0/9 = .000 | 2/9 = .222 |
| B1/B2 | 34/59 = .576 | 19/59 = .322 | 3/59 = .051 | 3/59 = .051 |
| B2/B2 | 88/180 = .489 | 44/180 = .247 | 17/180 = .094 | 31/180 = .172 |

[+]Denominator = total number of subjects with a given genotype (eg, A1/A1).

No significant differences in RFLP frequencies were found between DUS-assessed substance users and DIS-III-R-assessed users (for TaqI A1, $\chi^2=0.005$, ns; for TaqI B1, $\chi^2=0.331$, ns). We thus reanalyzed the data by pooling substance users assessed in both fashions for comparison with controls. Analysis of TaqI B1 data ($\chi^2=6.31$, p<0.02) and TaqI A1 data ($\chi^2=4.46$, p<0.04) again revealed significant associations.

Comparisons of TaqI A1 RFLP frequencies in ARC users and controls from all other published studies revealed significant associations when the controls were assessed ($\chi^2=15.41$, p<0.001), unassessed ($\chi^2=9.31$, p<0.003), or pooled ($\chi^2=14.80$, p<0.001).

To examine whether the effects noted could be attributed chiefly to the extent of alcohol intake, heavy alcohol users achieving DUS alcohol ratings of 3 were eliminated from the user group and reanalysis performed. Omitting heavy alcohol users did not significantly alter the elevated frequencies of the TaqI B1 RFLP found in the user group. 32.3% of all polysubstance users and 32.9% of the 73 polysubstance users free of heavy alcohol use displayed the TaqI B1 marker.

The hypothesis that individual differences in substance abuse may be due, in part, to different dopamine $D_2$ receptor alleles marked by Taq I RFLPs at the gene's 3' and 5' ends arises from initial work in alcoholics (K. Blum et al., JAMA 263, 2055–2060 (1990)). The hypothesis is strengthened by a compelling biological rationale for interactions between abused drugs and brain dopamine systems (G. Di Chiara and A. Imperato, Proc Natl Acad Sci U.S.A. 85, 5274–5278 (1988); R. A. Wise and P. P. Rompre, Annu Rev Psychol. 40, 191–225 (1989)). In the current example, significant associations with heavy substance use or abuse were found consistently for the TaqI B1 RFLP and less consistently for the TaqI A1 RFLP. These findings provide preliminary evidence that a more 5' TaqI RFLP (B1) may represent a better marker for a DRD2 gene variant possibly predisposing carriers to heavy substance use or abuse.

Selection of drug using and control populations provides opportunities for different approaches that could influence the results obtained. Many substance abusers use multiple psychoactive substances (D. R. Wesson et al., eds. *Polydrug Abuse: The Results of a National Collaborative Study*. New York, N.Y.: Academic Press, Inc.; 1978); 71% of the 192 DUS-assessed users in the current study reported moderate to heavy use of three or more different substances. To reflect this fact, we first studied subjects who frequently use multiple drugs, attempted to characterize each drug used by each subject, and analyzed data on the basis of overall lifetime peak use. This approach might provide a weaker test of linkage if only a single abused substance displayed such genetic association. For example, if only alcohol abuse contributed to the associations noted here, we might anticipate a weaker association between B1 RFLPs and substance abuse if individuals with heavy alcohol consumption were eliminated from our sample. In fact, elimination of heavy alcohol users (DUS rating=3) resulted in no decrease in the differences between the remaining DUS-assessed drug-abusing and control individuals for the TaqI B RFLP.

The characterization of these subjects also raises important issues of assessment type, validity and reliability. Errors in clinical assessment would weaken tests of the allelic association hypothesis. In addition, studying behaviors that could contribute to features of clinical diagnosis but might not reflect the behavioral impact of a DRD2 gene variant could yield false-negative results.

We originally began work with the DUS, an interview-based assessment of substance use that enabled approximate quantification of peak lifetime use for several types of substances and appeared to provide an assessment of a basic feature of substance abuse: level of substance consumption. Psychiatric genetic work using classical methods suggests that heavy substance use can show substantial genetic determinants (R. W. Pickens et al., Arch Gen Psychiatry 48, 19–28 (1991); C. R. Cloninger and T. Reich, In: Kety S. S., Rowland L. P., Sidman R. L., Matthysse S. W., eds. Genetics of neurological and psychiatric disorders. New York, N.Y.: Raven Press: 1983; pp. 145–166). Reliability and validity of the quantity-frequency approach to subjects' drug use were supported by the correlations between drug use assessments made on two occasions, assessments made with multiple instruments, and correlations with results of urine drug screens. However, several individuals who reported heavy use of various drugs did not fulfill criteria for DSM-III-R diagnoses of dependence or abuse on SCID or DIS-III-R assessments of the same drugs (S. S. Smith et al., "Validation of an instrument for quantifying drug use self-report: The ARC Drug Use Scale". Presented at the 53rd Annual Scientific Meeting. The Committee on Problems of Drug Dependence, Jun. 16–20, 1991, Palm Beach, Fla.).

We also evaluated subjects by determining lifetime psychiatric diagnoses of psychoactive substance use disorders using a structured psychiatric interview, the DIS-III-R, which can also demonstrate reliability and validity (J. E. Helzer et al., Arch Gen Psychiatry 42, 657–666 (1985); N. Oskooilar et al., DIS Newsletter 8, 9–10 (1991)).

Comparison of TaqI A and B RFLP frequencies in substance-using subjects failed to indicate significant differences between the quantity-frequency and psychiatric diagnosis approaches. These results suggested that we could combine subjects meeting criteria for DSM-III-R Substance Use diagnsoses with subjects reporting moderate to heavy drug use. It is still conceivable, however, that behavioral effects of a gene might be differentially reflected in quantity/frequency or in disease/disorder approaches to defining the affected group.

The RFLPs studied here are the result of polymorphic TaqI restriction sites in which "A" RFLPs are located ca. 9 kb 3' to the final exon of the $D_2$ receptor gene (O. Civelli, personal communication) and "B" RFLPs are located near the first coding exon (X. Y. Hauge et al., Genomics 10, 527–530 (1991)). These polymorphisms could have functional relevance if base pair differences directly influenced the gene's regulation. Alternatively, they could provide markers for structural or regulatory changes in other regions of the gene if these other changes and the TaqI variations were maintained together by linkage disequilibrium resulting in specific haplotypes (G. R. Uhl et al., Arch Gen Psychiatry 49, 157–160 (1992)). This linkage disequilibrium does exist (X. Y. Hauge et al., Genomics 10, 527–530 (1991); Dr. Bruce O'Hara et al, unpublished data). In our data, for example, the expected frequency of the A2/A2–B2/B2 haplotype would be 43% based on the frequencies of the A2 and B2 allelic markers. However, the observed frequency of this haplotype was 61% ($\chi^2$=16.33, p<0.0001) (76% for controls and 57% for users, $\chi^2$=5.15, p<0.03), indicating substantial linkage disequilibrium.

The lack of strong association between $D_2$ receptor gene RFLPs and substance use evident in this study is consistent with estimates of the heritable components of alcoholism and drug abuse (E. J. Devor and C. R. Cloninger, Annu Rev Genet. 23, 19–36 (1989); R. J. Cadoret et al., Arch Gen Psychiatry 43, 1131–1136 (1987)). One recent study of concordance rates for alcoholism in twin populations suggests that between 20 and 30% of the vulnerability to abuse or dependence on this substance may be genetic in origin (R. W. Pickens et al., Arch Gen Psychiatry 48, 19–28 (1991)). Attempts to link familial alcohol susceptibility to specific chromosomal markers and patterns of inheritance in families have not been consistent with a single genetic locus (S. B. Gilligan et al., Genet Epidemiol. 4, 395–414 (1987); C. E. Aston and S. Y. Hill, Am J Hum Genet. 46, 879–887 (1990)). The strong association between a single gene RFLP and alcoholism found by Blum et al. (K. Blum et al., JAMA 263, 2055–2060 (1990)) would thus fit poorly with this extent of heritability. The large environmental influences on expression of alcoholism, and their study of unrelated individuals rather than defined pedigrees also make the strength of their findings surprising.

To investigate the association between the DAT gene and substance abuse behaviors, one can make use of the variable number tandem repeat (VNTR) at the 3'-end of the mRNA described in example 1. Alternatively the TaqI RFLP described in example 2 could be utilized. In general, examination of VNTR markers is preferred, as such markers have a larger number of alleles and hence are "more informative", i.e. VNTR markers identify more subtypes than a regular "site-no site" RFLP marker. The same methodology described above for the study of the D2 dopamine receptor gene can be employed. As shown above, particular attention must be paid to the diagnostic criteria for identifying the abuse behavior if the results are to be meaningful.

To assess frequencies of the VNTR, DNA is obtained from leukocytes from research volunteers as described above. Genomic DNA (40 ng) is subjected to 35 cycles of amplification using AmpliTaq DNA Polymerase (1.25 U) and polymerase chain reaction with denaturing for 1 min at 93° C., and annealing/extension for 1 min at 72° C. in buffer supplied by the manufacturer (Perkin-Elmer). Oligonucleotides T3-5LONG (5'-TGTGGTGTAGGGAACGGCCTGAG-3', SEQ. ID. NO.:7) and T7-3aLONG (5'-CTTCCTGGAGGTCACGGCTCAAGG-3', SEQ. ID. NO.:8) are used at 0.5 uM final concentration. Reaction products are separated by 5% polyacrylamide gel electrophoresis, and product sizes estimated by comparison to molecular weight standards (BRL).

242 of the 254 chromosomes examined displayed either 9 or 10 copies of the 40 basepair repeat. Two chromosomes showed three copies, two showed 5 copies, three showed 7, four showed 8 and one showed 11 copies of the VNTR. Among individuals with 9 and/or 10 copies per chromosome there were racial differences in copy number frequencies. Whites displayed 30% and Blacks displayed 20% of the 9-copy variant. The 3' VNTR marker defined by 9 versus 10 copies of the 40 basepair repeat displayed no significant linkage disequilibrium with the more 5' TaqI RFLP ($\chi^2$ values were 5.51 and 4.62 for White and Black subjects, respectively, with 8 degrees of freedom, p>0.1.)

EXAMPLE 4
(predictive)
Expression of HUDAT protein in *Escherichia coli* and purification of the bacterially expressed protein Any of several expression systems can be utilized to obtain HUDAT protein expression in *E. coli*. For example, the plasmid vector pFLAG system (International Biotechnologies, Inc., New Haven, Conn.) produces the polypeptide of interest attached to a short protein sequence that allows purification of the fusion protein by use of a monoclonal antibody directed against a hydrophilic, and thus surface localized, octapeptide. The open reading frame midportion of the HUDAT cDNA is obtained by digestion of the pHCDAT7 plasmid with EcoRI and purification of the insert fragment encoding the HUDAT protein by electrophoresis and elution from an agarose gel by standard techniques. Oligonucleotides having the sequences 5'-GGGTCTAGACG-3' (SEQ. ID. NO.:9) and 5'-AATTCGTCTAGACCC-3' (SEQ. ID. NO.:10) are annealed to form an adaptor and the adaptor is ligated to the ends of the insert DNA. The ligation product is digested with XbaI and cloned into the XbaI restriction site of the pFLAG vector (International Biotechnologies, Inc.). The appropriate *E. coli* host is transformed and colonies containing the HUDAT CDNA may be screened by colony hybridization using the pcHUDAT as probe. Positive clones are grown as large-scale cultures and the fusion protein is obtained in pure form by use of the monoclonal antibody affinity column as described by the manufacturer of the system, except that the elution buffer is modified by the addition of 0.5% CHAPS (3-[(3-Cholamidopropyl)-dimethylammonio]1-propane-sulfonate). Authentic DAT protein lacking the FLAG octapeptide is obtained by enterokinase cleavage of the fusion protein as described by the supplier of the FLAG system.

EXAMPLE 5
(predictive)
Purification of DAT from tissues or from transformed mammalian cells As protein isolated from transformed bacterial cells lacks post-translational modifications, such as sugar additions, that occur in mammalian cells, the purification of the protein from tranformed COS cells is discussed.

COS cells transformed as described in (S. Shimada et al., Science 254, 576 (1991)) are subjected to a purification protocol as described for the purification of the GABA transporter (Radian, et al., J. Biol. Chem. 261, 15437–15441 (1987) with the modification that binding of labelled CFT is used to assay for the presence of DAT in the sample rather than labelled gamma-amino butyric acid. The protocol is modified as required to allow the isolation of DAT as a distinct protein by techniques known to a practitioner of the art.

EXAMPLE 6
(predictive)
Diagnosis of deficiency, mutant or overexpression of dopamine transporter by PCR mRNA obtained from tissue biopsy from a patient is converted subjected to quantitative reverse-transcript PCR (for example, see A. M. Wang, et al. PNAS U.S.A. 86:9717 (1989)) utilizing as primers oligonucleotides derived from the cDNA sequence of pcHUDAT. Use of the 5' 19-mer, GCTCCGTGGACTCATGTCTTC, bases 118 through 139 of FIG. 1 (SEQ. I.D. NO. 1) as the upstream primer and CACCTTGAGCCAGTGGCGG, the reverse complement of bases 1942 to 1960 of FIG. 1 (SEQ. I.D. NO. 1) as the downstream primer allows examination of the character of the protein coding region of the HUDAT MRNA. Variance in the expression level can be ascertained by comparison of product yield with a normal control. Abnormal mRNA structures can be diagnosed by observation of a product band of a length different from the normal control. Point mutants can be observed by use of primers and conditions appropriate for detection of the mismatch between the mutant and normal alleles. For example, the "reverse dot blot" procedure for screening the expression of several mutant alleles in a single experiment, which has been described for the CFTR gene, mutants of which cause cystic fibrosis (Erlich, H. A., et al Science 252:1643 (1991).

The HUDAT mRNA also contains a variable number tandem repeat element in the 3' untranslated portion of the mRNA which can be amplified for examination of an association between specific VNTR alleles and substance abuse behavior or diseases associated with expression of particular HUDAT alleles (See example 3).

EXAMPLE 7
(predictive)
Use of dopamine transporter expression to incorporate as part of overexpression of a panel of dopaminergic genes to reconstruct a dopaminergic cell line for therapy in human diseases resulting from defective dopamine transporter expression cDNAs for the human dopamine transporter, and for tyrosine hydroxylase and aromatic amino acid decarboxylase (DOPA decarboxylase) are transfected into cell types including COS cells as described above. Cells are cotransfected with the neomycin resistance marker, selected by growth in G418, and then tested for their ability to synthesize and accumulate dopamine. Individual subclones may be able to take up dopamine, without the ability to synthesize it. However, individual subclones are also likely to integrate several of the plasmids. If the plasmids cannot be introduced serially or together in this direction, serial edition of tyrosine hydroxylase and DOPA decarboxylase to stable cell lines already expressing the dopamine transporter stably should be employed (see above). The ability of cells to incorporate tritiated tyrosine into tritiated dopamine is tested via HPLC analysis and radiochemical detection as described (Uhl et al., Molecular Brain Research, 1991), their ability to take up tritiated dopamine is performed as described in the same reference.

These same procedures are used in transfecting cells obtained from an individual with a disease state caused by defects in dopamine transporter expression, either in the amount expressed or due to expression of a defective protein, so that stable immortalized cell lines expressing human dopamine transporter could be constructed with immunologic identity to the patient. Means of controlling the replication of these cells by encapsulating them in a matrix that is not porous to cell bodies, but able to be permeated by cell processes, or by use of inhibitory growth factors, can also be employed. A third strategy, temperature sensitive cell mutants that would not divide under physiologic temperatures (e.g. temperature sensitive COS cells variants) could be used to be able to express the dopaminergic cDNA stably, in a fashion that would produce dopaminergic cells. Each of these cell types are potential candidates for use in transplantation into striatum in individuals with striatal dopamine depletion in Parkinson's disease. Alternatively, genes could be incorporated with retroviral vectors as well-known for practitioners of the art.

EXAMPLE 8
(predictive)
Production of variant sequences in HUDAT protein and testing of their biological function Site directed mutagenesis using olgonucleotides is used to introduce specific single- and multiple-base changes into the HUDAT cDNA that change specific amino acids in the HUDAT protein. The ability of mutant transporters to take up [$^3$H] dopamine, [$^3$H] MPP+, and to bind [$^3$H] cocaine and cocaine analogues (especially [$^3$H] CFT) is tested as described previously (S. Shimada et al., Science 254, 576 (1991)). The Amersham mutagenesis system (version 2.1, technical bulletin code RPN1523) can be used. Initial studies of mutants of the aspartic acid residue in transmembrane domain 1, and the serine residues in transmembrane domain 7 of the rat DAT protein have revealed substantial effects on dopamine transport, and more modest effects on cocaine binding. These results document that the residues key to dopamine transport are not identical to those crucial to cocaine binding; the first transmembrane residue change of aspartic acid (residue 79) to glycine reduces cocaine binding by 10%, but reduces dopamine transport by over 95%. Mutations in the second extracellular domain in glycosylation sites help elucidate the role of glycosylation in the functions of this molecule (See also Example 9). Selective removal of the N and C terminal intracellular and second extracellular loop, and production of chimeric molecules with replacement of these regions with the corresponding regions of the GABA transporter further confirm the molecular features of DAT that are essential for dopamine transport and cocaine binding and allow development of agents dissociating the two processes.

EXAMPLE 9
(predictive)
Alteration of carbohydrate structure in the extracellular domain of the HUDAT protein As noted in example 1, the largest difference in the structure of the proteins predicted by the human and the rat dopamine transporter dDNA sequences is the absence of one of the four consensus sites for N-linked glycosylation of the protein (See FIG. 3). By virtue of their location in the same domain of the protein expected to most influence substrate binding, that is in the extracellular portion of the protein, it is of interest to investigate the contribution of the sugars to substrate binding. Site directed mutagaenesis can be performed as described for Example 8 introduce into the human DAT cDNA the asparagine residues to which N-linked sugars are attached and the remaining amino acids which constitute the glycosylation signal for that site that are found in the rat, but not the human CDNA. The result of expression of such mutant proteins can be evaluated by photo-affinity labelling of the protein and analysis by SDS-PAGE. Digestion of the protein with various glycosidases can be performed to assess the degree to which the pattern of glycosylation has been altered. as described by Lew et al. (R. Lew et al., Brain Research 539, 239 (1991)). For instance, compararison of the wild-type and mutant protein, both untreated and digested with N-glycanase, would should show similar sized proteins for the digested protein, but a larger protein for the untreated mutant, compared to the untreated wild-type protein if the introduction of the asparagine glycosylation signal resulted in successful incorporation of sugar into the protein at that site. More detailed information regarding the sugar structure can be obtained by exoglycosidase digestion experiments. For example, the presence of sialic acid residues in the polysaccharide can be detected by digestion with neuraminidase.

The influence of the polysaccarhide structure on function of the protein is then assessed by testing the properties of the the transporter using either stably transfected cells expressing the mutant protein, or by using cells transiently expressing the mutant transporter on their surface. The means for carrying out such functional studies are described by Shimada et al. (S. Shimada et al., Science 254, 576 (1991)).

EXAMPLE 10
(predictive)
Cell lines expressing HUDAT protein on the cell surface can be used to screen candidate compounds for efficacy as dopamine (or cocaine or functional analogs thereof) agonists or antagonists by evaluating the influence of the candidate compound upon the binding of dopamine (or cocaine or functional analogs thereof) to the surface of such cells. Another assay for dopamine agonist or antagonist activity is to measure the cytotoxicity to such cells of MPP$^+$ to such cells in the presence and absence of the candidate compound. Such assays are described using cells expressing the rat DAT cDNA in Shimada et al. (S. Shimada et al., Science 254, 576 (1991)) and can be applied as well to cells expressing the human DAT cDNA.

EXAMPLE 11
(predictive)
Production of antibodies to HUDAT and use of same in a diagnostic test for dopaminergic cell death
A. Production of polyclonal antibodies
HUDAT protein obtained as described above or synthetic polypeptides of amino acid sequence derived from the HUDAT sequence are used as immunogens in an appropriate animal. The serum is obtained from the immunized animal and either utilized directly or the antibody may be purified from the serum by any commonly utilized techniques. Polyclonal antibody directed only toward HUDAT can be isolated by use of an affinity column derivatized with the immunogen utilized to raise the antibody, again using techniques familiar to one knowledgable in the art.
B. Production of monoclonal antibodies to HUDAT Monoclonal antibodies to HUDAT or to particular epitopes of HUDAT may be produced by immunization of an appropriate animal with HUDAT protein obtained as above or with peptides of amino acid sequence derived from the HUDAT amino acid sequence. Hybridoma cultures are then established from spleen cells as described by Jaffe and McMahon-Pratt (Jaffe, C. L. and MacMahon-Pratt, D. J. Immunol. 131, 1987–1993 (1983)). Alternatively, peripheral blood lymphocytes may be isolated and immortalized by transformation with Epstein-Barr virus. These cells produce monoclonal antibodies, but if desired, hybridomas can then be made from the transformed lymphocytes (Yamaguchi, H. et al. Proc. Natl. Acad. Sci. 84, 2416–2420 (1987)). Cell lines producing anti-HUDAT antibodies are identified by commonly employed screening techniques. Monoclonal antibody is then purified by well known techniques from the supernatants of large-scale cultures of the antibody producing cells.
C. Diagnosis of dopaminergic cell death in vivo by immunoassay of cerebrospinal fluid of a patient using anti-HUDAT antibodies The death of dopaminergic neurons in the brain of a patient should result in the accumulation in the cerebrospinal fluid, which bathes these cells, of membrane debris as a product of lysis of the dead cells. Other pathologic conditions, short of cell death that result in the release of DAT protein, or degraded peptide fragments of HUDAT protein into the surrounding medium can also be imagined. The cerebospinal fluid can be sampled by lumbar puncture of a patient. The presence of degradation products of HUDAT protein is detected by immunoassay, using as the primary antibody at least one of the products obtained as described above. Elevated levels of HUDAT protein detected in the cerebrospinal fluid, compared with the range seen in normal controls is indicative of Parkinsons's disease or drug-induced neurotoxicity. Alternatively, disease progression can be monitored by the assessment of HUDAT levels in serial samples from the same patient.

What is claimed is:

1. An isolated cDNA comprising a nucleotide sequence which encodes a protein having the amino acid sequence set forth in SEQ. I.D. NO. 2, wherein said protein selectively binds to dopamine, cocaine or a compound which demonstrates displacement of [$^3$H]-labelled CFT from dopamine transporter or striatal membrane preparations.

2. A eukaryotic cell line derived from a cell type that does not normally express dopamine transport activity at its surface that has been made to transport dopamine or to bind CFT by the introduction of the DNA of claim 1 into its genome.

3. The cell line of claim 2 wherein the cell type is COS cells.

4. A recombinant DNA plasmid comprising the cDNA of claim 1, a replication DNA fragment that provides for replication of said recombinant DNA in a prokaryotic cell, a promoter DNA fragment that provides for transcription of the cDNA in a prokaryotic cell, and a translation DNA fragment that provides for translation in a prokaryotic cell of mRNA transcribed from said cDNA, said cDNA and DNA fragments being operatively linked so as to provide for expression of said cDNA when said plasmid is introduced into a prokaryotic cell.

5. A recombinant DNA plasmid comprising the cDNA of claim 1, a replication DNA fragment that provides for replication of said recombinant DNA in a eukaryotic cell, a promoter DNA fragment that provides for transcription of the cDNA in a eukaryotic cell, and a translation DNA fragment that provides for translation in a eukaryotic cell of mRNA transcribed from said cDNA, said cDNA and DNA fragments being operatively linked so as to provide for expression of said cDNA when said plasmid is introduced into a eukaryotic cell.

6. An isolated cDNA comprising the nucleotide sequence of SEQ. ID. NO.:1.

7. An isolated cDNA comprising a DNA fragment having a nucleotide sequence which encodes the amino acid sequence of SEQ. I.D. NO. 2 and further comprising a repetitive element in a 3' untranslated portion of said cDNA, wherein said repetitive element comprises head-to-tail repeats of a nucleotide sequence that is at least 90% identical to the sequence shown in SEQ. I.D. NO. 3.

8. An isolated cDNA of claim 7 having the nucleotide sequence of SEQ. I.D. NO. 1.

9. A recombinant DNA plasmid comprising the cDNA of claim 7, a replication DNA fragment that provides for replication of said recombinant DNA in a prokaryotic cell, a promoter DNA fragment that provides for transcription of the cDNA in a prokaryotic cell, and a translation DNA fragment that provides for translation in a prokaryotic cell of mRNA transcribed from said cDNA, said cDNA and DNA fragments being operatively linked so as to provide for expression of said cDNA a when said plasmid is introduced into a prokaryotic cell.

10. A recombinant DNA plasmid comprising the cDNA of claim 7, a replication DNA fragment that provides for replication of said recombinant a eukaryotic cell, a promoter DNA fragment that provides for transcription of the cDNA in a eukaryotic cell, and a translation DNA fragment that provides for translation in a eukaryotic cell of mRNA transcribed from said cDNA, said cDNA and DNA fragments being operatively linked so as to provide for expression of said cDNA when said plasmid is introduced into a eukaryotic cell.

\* \* \* \* \*